(12) United States Patent
Buckenham et al.

(10) Patent No.: US 11,517,853 B2
(45) Date of Patent: Dec. 6, 2022

(54) SYSTEM FOR PROCESSING OF BIOGAS TO PRODUCE ELECTRICITY IN FUEL CELLS

(71) Applicant: California Bioenergy LLC, Dallas, TX (US)

(72) Inventors: N. Ross Buckenham, Dallas, TX (US); Daniel Waineo, Portland, OR (US)

(*) Notice: Subject to any disclaimer, the term of this patent is extended or adjusted under 35 U.S.C. 154(b) by 489 days.

(21) Appl. No.: 16/783,940

(22) Filed: Feb. 6, 2020

(65) Prior Publication Data
US 2020/0259197 A1    Aug. 13, 2020

Related U.S. Application Data

(60) Provisional application No. 62/802,502, filed on Feb. 7, 2019.

(51) Int. Cl.
*H01M 4/02*   (2006.01)
*B01D 53/52*  (2006.01)
(Continued)

(52) U.S. Cl.
CPC ............ *B01D 53/52* (2013.01); *A01C 3/00* (2013.01); *A61L 11/00* (2013.01); *B01D 53/04* (2013.01);
(Continued)

(58) Field of Classification Search
CPC ....................................................... H01M 4/02
See application file for complete search history.

(56) References Cited

U.S. PATENT DOCUMENTS 3,933,628 A   1/1976 Varani
4,100,023 A   7/1978 McDonald
(Continued)

FOREIGN PATENT DOCUMENTS

CN   204029930 U   12/2014
CN   206916094 U    1/2018
(Continued)

OTHER PUBLICATIONS

"Economic Feasibility of Dairy Digester Clusters in California: A Case Study", Prepared by California Dairy Campaign For the United States Department of Agriculture (USDA), Rural Development Agency, Value Added Producer Grant (VAPG) Program; Jun. 2013, 66 pages.
(Continued)

*Primary Examiner* — Jacob B Marks
(74) *Attorney, Agent, or Firm* — Stephen Y. Liu; Carstens, Allen & Gourley, LLP

(57) ABSTRACT

A system including biogas purification and provides biogas as feedstock to a solid oxide fuel cell. The biogas purification treatment process provides a polished biogas that is substantially free of carbonyl sulfides and hydrogen sulfide. The system uses a biogas treatment apparatus, that includes apparatus such as a packed columns, comprising copper oxide or potassium permanganate packing material, and an activated carbon component configured to treat the biogas by polishing it to remove carbonyl sulfides and deleterious trace residues, such as hydrogen sulfide, that were not removed by any prior bulk H2S removal steps. In addition, an oil removal device is used to remove any entrained fine oil droplets in the biogas. A polished biogas having in the range of 60% methane is charged to the fuel cell. Electricity generated may be fed into a grid or used directly as energy to charge electrical-powered vehicles, for example. Energy credits are tracked in real time and are appropriately assigned.

20 Claims, 11 Drawing Sheets

(51) Int. Cl.
| | |
|---|---|
| *H02J 3/38* | (2006.01) |
| *H02J 7/34* | (2006.01) |
| *H01M 8/0668* | (2016.01) |
| *H01M 8/0662* | (2016.01) |
| *B01D 53/04* | (2006.01) |
| *B01D 53/22* | (2006.01) |
| *G05B 19/418* | (2006.01) |
| *A01C 3/00* | (2006.01) |
| *A61L 11/00* | (2006.01) |
| *H01M 8/12* | (2016.01) |
| *C02F 1/52* | (2006.01) |
| *C02F 11/18* | (2006.01) |

(52) U.S. Cl.
CPC .......... *B01D 53/229* (2013.01); *C02F 1/5236* (2013.01); *C02F 11/185* (2013.01); *G05B 19/418* (2013.01); *H01M 8/0668* (2013.01); *H01M 8/0675* (2013.01); *H01M 8/12* (2013.01); *H02J 3/381* (2013.01); *H02J 7/34* (2013.01); *B01D 2251/304* (2013.01); *B01D 2251/604* (2013.01); *B01D 2253/102* (2013.01); *B01D 2253/1122* (2013.01); *B01D 2257/304* (2013.01); *B01D 2258/05* (2013.01); *B01D 2259/45* (2013.01); *G05B 2219/32287* (2013.01); *H02J 2300/30* (2020.01)

(56) References Cited

U.S. PATENT DOCUMENTS

| | | |
|---|---|---|
| 4,750,454 A | 6/1988 | Santina et al. |
| 5,269,634 A | 12/1993 | Chynoweth et al. |
| 5,476,994 A | 12/1995 | Trezek |
| 6,474,267 B1 | 11/2002 | Padgett |
| 6,523,129 B1 | 2/2003 | Tressler et al. |
| 6,824,682 B2 | 11/2004 | Branson |
| 6,852,225 B1 | 2/2005 | Oswald et al. |
| 6,855,253 B2 | 2/2005 | Baumgartner et al. |
| 8,017,013 B2 | 9/2011 | Kotelko et al. |
| 8,211,211 B1 | 7/2012 | Knaebel |
| 8,221,626 B2 | 7/2012 | Sassow |
| 8,632,024 B2 | 1/2014 | Gitschel et al. |
| 8,658,026 B2 | 2/2014 | Foody et al. |
| 8,753,854 B2 | 6/2014 | Foody |
| 8,945,373 B2 | 2/2015 | Foodt |
| 9,005,337 B2 | 4/2015 | Grill |
| 9,005,442 B2 | 4/2015 | Reid |
| 9,039,807 B2 | 5/2015 | Mitariten et al. |
| 9,040,271 B2 | 5/2015 | Foody |
| 9,108,894 B1 | 8/2015 | Foody et al. |
| 9,146,547 B2 | 9/2015 | Sharma et al. |
| 9,181,564 B2 | 11/2015 | Leonetti et al. |
| 9,222,048 B1 | 12/2015 | Foody |
| 9,323,238 B2 | 4/2016 | Buckenham |
| 9,447,353 B2 | 9/2016 | Foody |
| 9,464,571 B2 | 10/2016 | Kremer et al. |
| 9,508,085 B2 | 11/2016 | Foody |
| 9,514,464 B2 | 12/2016 | Foody |
| 9,643,867 B2 | 5/2017 | Brooks et al. |
| 9,644,160 B2 | 5/2017 | Brotherton et al. |
| 9,690,275 B2 | 6/2017 | Gan et al. |
| 9,969,949 B1 | 5/2018 | Food et al. |
| 10,093,540 B2 | 10/2018 | Foody |
| 10,202,622 B2 | 2/2019 | Foody et al. |
| 10,266,440 B2 | 4/2019 | Assadi et al. |
| 2002/0056690 A1 | 5/2002 | Wegner |
| 2002/0114866 A1 | 8/2002 | Kartchner |
| 2004/0188356 A1 | 9/2004 | Haydock |
| 2005/0120715 A1 | 6/2005 | Labrador |
| 2006/0243648 A1 | 11/2006 | Shain et al. |
| 2007/0254196 A1 | 11/2007 | Richards et al. |
| 2008/0035561 A1 | 2/2008 | Gray (Gabb) et al. |
| 2009/0090679 A1 | 4/2009 | DeWaard |
| 2010/0044279 A1 | 2/2010 | Tucker |
| 2010/0105127 A1 | 4/2010 | Ginsburg |
| 2010/0148585 A1 | 6/2010 | Adam et al. |
| 2010/0236253 A1 | 9/2010 | Adam |
| 2011/0023497 A1 | 2/2011 | Assmann |
| 2011/0042307 A1 | 2/2011 | VanOrnum et al. |
| 2011/0126601 A1 | 6/2011 | Bottchar |
| 2011/0259805 A1 | 10/2011 | Standley et al. |
| 2012/0000357 A1 | 1/2012 | Roe et al. |
| 2013/0024014 A1 | 1/2013 | Sharma et al. |
| 2013/0073098 A1 | 3/2013 | Gan et al. |
| 2013/0122575 A1 | 5/2013 | Revankar Krishna Prasad |
| 2013/0199185 A1 | 8/2013 | Wain et al. |
| 2013/0225885 A1 | 8/2013 | Foody et al. |
| 2013/0238158 A1 | 9/2013 | Gan et al. |
| 2013/0252120 A1 | 9/2013 | Roertson |
| 2013/0266997 A1 | 10/2013 | Hickey et al. |
| 2014/0015323 A1 | 1/2014 | Matthews |
| 2014/0039708 A1 | 2/2014 | Curtis et al. |
| 2014/0222698 A1 | 8/2014 | Potdar et al. |
| 2014/0294719 A1 | 10/2014 | Schreiner |
| 2014/0352332 A1 | 12/2014 | Mann et al. |
| 2015/0119623 A1 | 4/2015 | Huang |
| 2016/0160239 A1 | 6/2016 | Hoff |
| 2016/0241109 A1 | 8/2016 | Buckenham |
| 2017/0313952 A1 | 11/2017 | Kennedy |

FOREIGN PATENT DOCUMENTS

| | | |
|---|---|---|
| GB | 2301112 A | 11/1996 |
| WO | WO2015073963 A1 | 5/2015 |
| WO | WO 2005050768 A1 | 6/2015 |

OTHER PUBLICATIONS

Zhao, et al., "Purification Technologies for Biogas Generated by Anaerobic Digestion", CSANR Research Report 2010-001, Climate Friendly Farmng, Ch. 9, Compressed Biomethane, 24 pages.

DMT Clear Gas Solutions; Jan. 5, 2017; Offer California BioEnergy 750 and 2000 scfm biogas to CNG plant, 22 pages.

Kowitt, Beth, "How A Huge Dairy Is Solving A Major Pollution Problem", Fortune, Jan. 27, 2016, <http://amp.timeinc.net/fortune/2016/01/27/fair-oaks-dairy-farm-manure-fuel>, 19 pages.

CPS 12 Blend Absorbent Media, PureAir Filtration, 1 page.

Linnane, "FuelCells shares rocket 108% on news of expanded carbon capture deal with Exxon", MarketWatch, Nov. 7, 2019, 3 pages.

Zhao, et al., "The Hydrolysis of Carbonyl Sulfide at Low Temperature: A Review", Hindawi Publishing Corporation, The Scientific World Journal, vol. 2013, Article ID 739501, 9 pages.

Sattler, et al., "Removal of Carbonyl Sulfide Using Activated Carbon Adsorption", Journal of the Air & Waste Management Association; ISSN 1047-3289 J. Air & Waste Manage. Assoc. 56:219-224, Feb. 28, 2012, <https://www.tandforline.com/action/journalInformation?journalCode=uawm20>, 7 pages.

"Chapter 3: Integration of Variable Energy Resources", MIT Study on the Future of the Electric Grid, 24 pages.

"Appendix B: Electric Power System Basics", MIT Study on the Future of the Electric Grid, 18 pages.

Mukhtar et al.;"Solid-Liquid Separation of Animal Manure and Wastewater"; AgriLIFE EXTENSION, Texas A&M System, E13, 9-99; 6 pages.

CN 206916094_machine translation.

CN 20140294719_machine translation.

Shelford, T. et al., "Farmer's Guide to Dairy-Derived Biogas Production, Treatment and Utilization"; University of Maryland Department of Environmental Science & Technology, Oct. 1, 2018 downloaded on Mar. 24, 2020 from http://www.gcedonline.com/agribusinesss; p. 27 Safety monitoring section; p. 29, first paragraph.

US Department of Energy, "Novel Sorbent to Clean Biogas for Fuel Cell CHP"; OSTI Identifier 1222699; Sep. 2016; entire document.

Search Report and Written Opinion issued by ISA/US for International Application No. PCT/US2020/016992 dated Apr. 14, 2020.

(56) References Cited

OTHER PUBLICATIONS

Search Report and Written Opinion issued by ISA/US for International Application No. PCT/US2020/017050 dated Apr. 27, 2020.

Dairy BioGas Conditioning

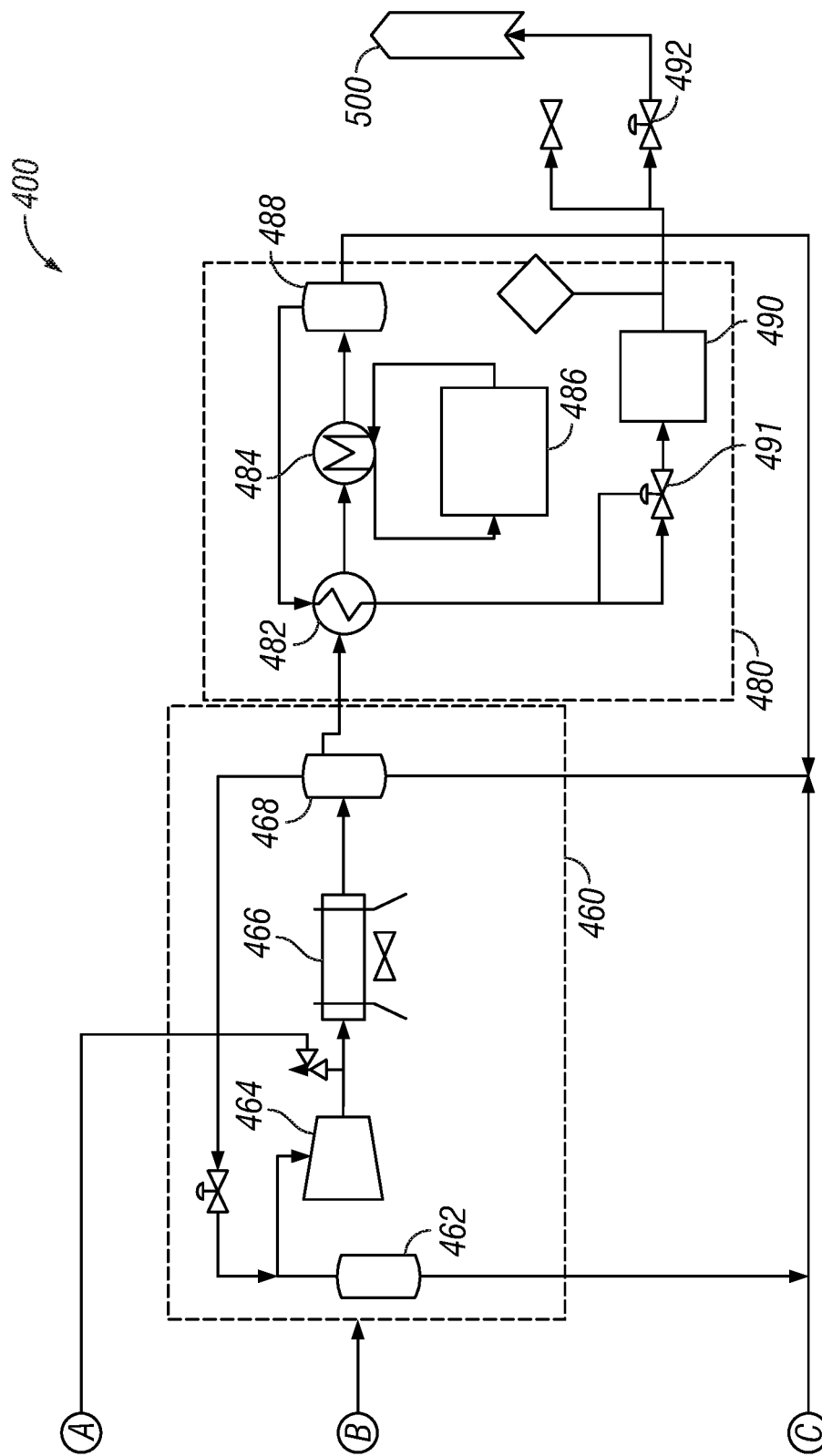

BioGas to BioMethane Upgrader

SYSTEM FOR PROCESSING OF BIOGAS TO PRODUCE ELECTRICITY IN FUEL CELLS

CROSS-REFERENCE TO RELATED APPLICATION

The present disclosure claims priority to U.S. Provisional Patent Application No. 62/802,502, filed Feb. 7, 2019, all of which is incorporated herein by reference in its entirety for all purposes.

FIELD OF THE INVENTION

The technology relates to the field of biogas conversion to biomethane for energy generation, and more particularly relates to the collection of biogas from a plurality of sources generating biogas from decomposition of organic waste, at a range of geographic locations, and routing the collected biogas to location(s) for processing into biomethane and/or generation of electricity, including generation of electricity in fuel cells.

DESCRIPTION OF THE RELATED ART

Electricity is a necessary power source in a modern technology-based economy, and also in those economies that are developing into modern economies, which have exhibited a great demand for more electric power as standards of living improve. Initially, the basic source for electricity generation was combustion of coal (carbon), or oil (hydrocarbons), both of which are often called "fossil fuels." Both coal and hydrocarbon oils generate carbon dioxide as a combustion byproduct, and carbon dioxide is a greenhouse gas that contributes to the phenomenon of global warming, or climate change.

Electricity has also been generated as hydro-electric power by turbines driven by flow of water, typically at dams when water is released through sluice gates to drive the turbines. More recently, there has been an upsurge in generation of electricity using solar power as the cost of solar cell panels have begun to decline thereby reducing the cost per KW-hr of electricity generated. In addition, the use of wind power turbines, especially in Texas and California, has caused electricity from wind power to become a significant part of the supply to the power grid. Solar and Wind both suffer the disadvantage of being intermittent (not schedulable) sources of electricity.

There also continues to be growing interest in both small as well as large scale generation of biogas (typically 60% methane) that can be purified into a "renewable natural gas" or RNG, a more purified combustible gas (generally at least 95% pure methane) from waste. Ordinarily, this biogas is a natural product of the decomposition of organic waste material, most often though an anaerobic process, and is released into the atmosphere. In the atmosphere, it is believed that biogas, especially the methane component, is a "greenhouse gas" that contributes to the phenomenon of global warming, or climate change. On the other hand, if the biogas could be captured and treated to generate electricity or processed into RNG, this methane gas could be used to generate power in methane-burning power plants or fuel compressed natural gas vehicles with the previously vented methane being destroyed in the process thus eliminating its greenhouse gas effect. Moreover, the substitution of bio-derived gas for transportation fuels, such as compressed natural gas ("CNG") presents a further opportunity to back out fossil fuel combustion and thereby reduce greenhouse gas emissions.

Methane has a lower carbon to hydrogen ratio than coal or hydrocarbon oils. Thus, methane produces less carbon dioxide upon combustion. As a result the net effect of this capture of methane, and subsequent combustion to produce electricity, is to "back out" other fuel sources that would have been combusted in the power plants, such as coal or hydrocarbon oils. This is highly beneficial since the combustion of methane produces less carbon dioxide per KW-hr of electricity or less carbon dioxide per brake horsepower-hour of a vehicle engine, than the combustion of other hydrocarbon fuels because of its lower carbon to hydrogen ratio. Thus, the removal of the biogas preventing release into the atmosphere, and the combustion of methane from the biogas provides energy has a two-fold benefit in reducing greenhouse gas emissions: reduction of biogas into the atmosphere, and less combustion of carbon dioxide emissions in electricity generation by "backing out" coal or other hydrocarbons that have a higher carbon to hydrogen ratio. Moreover, organic waste generation and decomposition to produce biogas are continuously ongoing processes, so that biogas is, in that sense, a potentially continuously "renewable" energy supply.

SUMMARY

The technology presented herein provides access to remote biogas sources ("digesters") that are geographically widely distributed, predicts (based on instrumentation) the availability and quality of biogas from these remote sources typically 24 hours in advance, conditions and prepares the biogas to safely aggregate the biogas via a network of conduits and conveys the biogas to biogas consuming devises ("generators") and/or to a single treatment facility where it is converted to RNG or biomethane and controlledly compressed into a natural gas pipeline for subsequent use as combustion fuel, compression to CNG or LNG (liquified natural gas) for vehicle fuel use, or use in fuel cells to create electricity directly. Electricity generated at the treatment facility, or at the remote biogas sources, can be used directly or indirectly (via a contract rather than physical delivery of electrons) to provide a renewable source of electrical energy for plug-in battery-powered electric vehicles (PEVs), thereby providing the desirable goal of converting biogas to clean transportation energy.

In an exemplary embodiment there is provided a biogas production, conditioning, collection, electrical generation, purification and delivery system. The system aggregates biogas from a plurality of remote sources and treats the biogas to produce electricity and/or biomethane. The system comprises: a network of conduits configured to convey biogas from the plurality of remote sources of the biogas based on a monitored or automatically detected availability and quality of biogas at each respective remote source. A biogas compressor at each of the remote locations is controlled by a central controller that utilizes data that includes biogas availability and quality data. The central controller is configured to instruct the remote biogas compressor(s) to supply compressed biogas to several potential processes, as well as to a central biogas processing facility, depending upon input data. Thus, the biogas may be compressed to a fuel cell or to an internal combustion engine powered generator for direct conversion of the biogas to electricity to power at least some of the equipment at the remote source or at the centralized facility, or the electricity can be transmitted to a charging station for PEVs to charge vehicle batteries. Compressed biogas can also be supplied to a biogas header that conveys the biogas to the central processing facility. Here, the received biogas from many remote sources in the network of linked-together plurality of remote sources is treated and processed from biogas into biomethane and/or also converted to electricity pre (as biogas fuel) or post upgrading (as biomethane fuel). The central processing facility has an input compressor that is controlled by the central controller that operates based on data including the data from the remote sources about the availability of biogas at the sources. The central treatment facility includes several biogas treatment operations, including but not limited to a biogas hydrogen sulfide removal stage; an activated carbon scrubber (which may be downstream from the hydrogen sulfide removal stage); a carbon dioxide removal stage (which may be) downstream from the hydrogen sulfide removal stage for purifying the biogas into biomethane by removal of carbon dioxide. And the central processing facility also has a biomethane gas compressor for compressing the produced biomethane, also under control of the central controller. Thus, the biomethane may be charged to a generator such as a fuel cell for direct conversion of the biomethane to electricity to power at least some of the equipment at the treatment facility, or the electricity and/or its environmental attributes can be transmitted (e.g. directly or virtually via a contract) to a charging station for PEVs to charge vehicle batteries. The biomethane can also be charged to a system for compression to renewable compressed natural gas (R-CNG) for use as a vehicle fuel. Or, the biomethane can be compressed to a natural gas pipeline, as explained in more detail here below. The decision (and control) of the biomethane disposition to the natural gas pipeline or to CNG or to fuel cells to create electricity for PEVs is based on several control variables including biogas availability, projected biogas availability, quality, quantity, moisture content, presence or absence of contaminants, hydrogen sulfide levels, oxygen levels, nitrogen levels, historical production rates, projected generator or upgrading plant demand rates, upcoming system maintenance inputs, digester status, digester feedstock availably, ambient temperature and digester efficiency factors, current biogas storage levels and remaining biogas storage levels.

The sources of biogas may include organic animal waste anaerobic digesters, such as for example dairy farm animal waste, and/or captured biogas from waste water treatment plant digesters, special purpose organic waste or mixed substrate digesters, landfills and or combinations of these sources.

The plurality of sources of biogas of the exemplary embodiment may include biogas sources located remote from each other, and the network of conduits enable fluid communication between the remote sources and a central biogas header that is the portion of the network carrying biogas to be received at the central processing facility.

A consideration to bear in mind is that to safely and efficiently convey biogas in a conduit it is (likely) necessary to "condition" the biogas to remove most of its hydrogen sulfide and water prior and in some cases its carbon dioxide prior to its insertion into the gathering/collection line. This conditioning of the biogas will occur at or close to the digester source and prior to compression into the gathering or collection line. If the biogas is utilized by an internal combustion engine or fuel cell generator directly from the gathering line it may need further polishing to remove all traces of contaminants such as hydrogen sulfide or siloxanes.

The biogas hydrogen sulfide removal stage of the central processing facility of the exemplary embodiment may include a sodium hydroxide gas scrubber or an iron sponge column.

At least some of the sources of biogas of the exemplary embodiment may include a gas quality sensor (measuring and logging for example the percent of methane, oxygen, carbon dioxide, moisture, hydrogen sulfide) and a gas quantity flow meter. The quantity and quality of the energy exported form each digester feeds the control system and also the accounting system for allocation of payments back to the owner or landlord hosting the digester. A hydrogen sulfide sensor located to confirm quality is acceptable and/or to detect release of hydrogen sulfide into a surrounding vicinity of the at least some of the sources and activate a central controller to shut a valve to cut off flow of biogas, as necessary, to eliminate or minimize leakage upon detection of hydrogen sulfide gas. It is also important to detect hydrogen sulfide for other reasons: hydrogen sulfide poisons upgrader membranes or pressure swing absorbents, poisons fuel cells, and damages internal combustion engines. So, the sensor should supply input to the control system to confirm acceptable quality. [Currently in California the collection line, by permit and safety considerations, cannot have >10 ppm H2S (sometimes up to 100 ppm H2S is OK, typical biogas is 2000-5000 ppm H2S.]

The remote sources of biogas may each include a flow sensor configured to detect a flow of biogas from the source. The flow sensor data is transmitted to a central controller that controls a valve, such as a three-way valve, to recycle a portion of the flow back to the respective source of biogas. The remote sources (digesters) may include a gas chromtograph or other form of gas analyzer supplying data to the control system to ensure the quality of the biogas is acceptable for delivery to the collection system and delivery ads a fed gas to the generators and/or to the upgrading plant(s). The remote source may include a flow meter also providing data to the control system to measure the flow quantity of gas for control purposes and also for accounting of the digester production of energy and its quality into the system.)

At least one of the plurality of biogas sources of the exemplary embodiment may include a flexible roof over the waste digester. The flexible roof expands upward when an amount of generated biogas in the digester increases and biogas pressure increases under the flexible roof. The biogas source may have an automatic detection device that provides data about the amount of biogas available from the digester, such as but not limited to, a laser deflection measurement apparatus. The apparatus may be positioned and configured to measure a degree of deflection of the flexible roof as it moves under biogas pressure. The measured laser deflection data is transmitted to the central controller that controls a compressor that draws biogas from the digester of the respective biogas source based on the data that includes data about biogas availability. Alternatively, or in addition, biogas availability can also be estimated by periodic human inspection. These inspections could be weekly, daily or several times per day depending on the production rate and remaining storage capacity of the digester. Thus, from observation, if the roof is "highly deflected upward," more biogas is available. Conversely, when the roof deflection is lower and/or declining, less biogas is available.

There is also presented an exemplary biogas purification apparatus and method used in conjunction with a fuel cell for directly converting biogas to electricity. The biogas supply to the biogas purification system may be from the central biogas processing facility also described herein where some purification of raw biogas has already taken place and where the exiting biogas has a reduced concentration of compounds such as H2S and other sulfur compounds, as well as reduced moisture content. This biogas is the source gas for further purification by removal of deleterious compounds to provide a biogas that is a suitable fuel cell feedstock. Typically, but not necessarily, the biogas may contain about 60% or more methane, along with CO2 as a large component.

The fuel cells useful include those fuel cells adapted to generation of electricity directly from methane. Solid Oxide ("SOFC") fuel cells, for example, are able to convert an input of methane gas to electricity that could be input to the electrical grid or used to charge electrical vehicles (EVs) or batteries, or for any other purpose, such as driving compressors, pumps and other equipment.

Fuel cells typically require a methane feedstock free of chemicals that would be deleterious to the cell and also prefer a continuous methane feed varying between 20% and 100% of the fuel cell capacity for efficient operation and to maintain the required operating temperature. Accordingly, while the flow rate of the biogas supply to the fuel cell might be variable over time, care should be taken to avoid a "low flow" condition that drops below the minimum turndown rate of the cell that might cause an interruption in cell operation. The exemplary biogas purification apparatus provided has an input of biogas (raw biogas that has already been pretreated to remove the bulk of the hydrogen sulfide) and further treats ("polishes") the biogas to remove sulfurous compounds, including carbonyl sulfides (COS), which are deleterious to the fuel cell.

There is provided a continuous system of producing electricity directly from biogas. The system includes at least one, and in some cases a plurality of animal manure digester (s). The digesters produce a raw digester biogas comprising methane, carbon dioxide and sulfur compounds, and also usually contain varying amounts of the gas components of air or oxygen, either accidentally drawn into the digester, or deliberately added to the digester for purposes such as to assist aerobic bacteria to remove H2S and other sulfur compounds from the digester gas, while the biogas is still in the digester. The digester gas may be fed directly to a biogas treatment system for removal of the bulk of the H2S and then to a biogas purification system before being charged directly to a fuel cell. The biogas purification apparatus is configured to continuously treat the biogas to remove residual H2S as well as other sulfur compounds, such as COS, that are potential fuel cell poisons, from the biogas or the biomethane as the case may be. It should be noted that the fuel cell can also be charged with biogas from the central processing facility, described elsewhere herein) bypassing the gas purification system, provided that the biogas is substantially free of contaminants such as COS and H2S that might poison the fuel cell.

The biogas purification and electricity generation system optionally includes apparatus (or a method if this is achieved by "a book and trade" of the renewable energy credits (RECs) and electricity from grid injection) to utilize the fuel cell-produced electricity to charge electrical vehicles; and in that event the system is configured to measure, record and transmit data about the amount of electrical energy used to charge electrical vehicles. This can be transmitted in real time to a cloud-based computer system so that a determination can be made from the data of units of electrical charge produced per unit of biogas, and units of electrical charge received by EVs and other users. From this data, an amount of renewable energy credits attributable to conversion of biogas to electricity can be calculated and apportioned.

The exemplary biogas purification system can operate using a variety of sources of biogas, and the digesters at the plurality of remote sources of biogas can be digesters of any suitable animal manure, including without limitation, cow manure chicken manure, or pig manure or horse manure. Advantageously, when sourced from cow manure, the biogas is free of siloxanes, which is deleterious to fuel cells. The biogas purification treatment process provided herein provides a treated biogas that is substantially free of carbonyl sulfides or has such low trace amounts of carbonyl sulfide that these are not deleterious to operation of the fuel cell. In an exemplary embodiment, the system uses a biogas treatment apparatus, such as a packed columns, comprising copper oxide or potassium permanganate, and an activated carbon component configured to treat biogas by polishing it to remove carbonyl sulfides and deleterious trace residues, such as hydrogen sulfide, that were not removed by any prior bulk H2S removal steps. In addition, a gas demister may be deployed in the biogas purification apparatus to remove any entrained fine oil droplets in the biogas in order to protect any components of the biogas polishing apparatus and the fuel cell from the deleterious effects of oil incursion.

The fuel cell system also may include apparatus to convert a direct electrical current produced by the solid state fuel cell to alternating current and apparatus to feed alternating current to an electrical grid.

The fuel cell of system can be any of a variety of fuel cells suitable to convert methane to electricity. An example is the solid oxide fuel cell that can be configured to process biogas to carbon dioxide and water while producing electricity. The condensate formed from conversion of the methane of the biogas to electricity in the fuel cell can be recycled (or disposed of) on the farm that is providing the manure. The (clean) CO2 waste from the fuel cell could be vented, or used in a green house, or other plant growing operation, to enhance the growth of plant, algae or other CO2 consuming photosynthesis-based life form.

The biogas purification system may include a flow control apparatus that includes a biogas holdup tank configured to buffer variations in biogas flow rate into the system or to retain a buffer so that if there is any interruption in supply, the buffer can be used to smooth out the biogas delivery rate to the fuel cell, maintain the flow rate above the minimum turndown rate, and maintain fuel cell operating temperature. These variations in biogas flow rate may reflect variations in digester gas flow rate from the digester. Preferably, the digesters have a bladder configuration, as described herein. The system has a compressor which may be used to compress biogas into the holdup tank, and an electronic controller is configured to maintain a continuous steady biogas flow to the solid state fuel cell, even as flow of raw digester gas from the digester varies over time. The controller may be configured to make step changes in biogas flow rate to the solid state fuel cell based on data that may include detected biogas availability.

The biogas purification system may be configured such that the solid state fuel cell operates at 80 to 100% of capacity, where it is most efficient. The treated biogas charged to the fuel cell comprises up to 40 mol. % carbon dioxide and is free of sulfurous compounds, meaning that the level of sulfur and sulfurous compounds is so low as to not adversely affect the operation of the fuel cell during a normal operational cycle. The system is configured such that the solid state fuel cell operates at temperatures in the range about 500 to about 1000° C., preferably in the range about 500 to about 750° C., or less than about 750° C.

The system is configured to deliver a continuous supply of fuel within the range of 205 to 80% of the capacity of the fuel cell such that the fuel cell is always on, remains hot and does not have to be turned off, restarted, or lose its minimum operating temperature.

The foregoing presents a brief and non-comprehensive summary of some aspects of the technology that is further explained in more detail, here below.

BRIEF DESCRIPTION OF THE DRAWINGS

The foregoing aspects and many of the attendant advantages of the present technology will be more readily appreciated by reference to the following Detailed Description, when taken in conjunction with the accompanying simplified drawings of exemplary embodiments. The drawings, briefly described here below, are not to scale, are presented for ease of explanation and do not limit the scope of the inventions recited in the accompanying patent claims.

DETAILED DESCRIPTION

Figure 1:
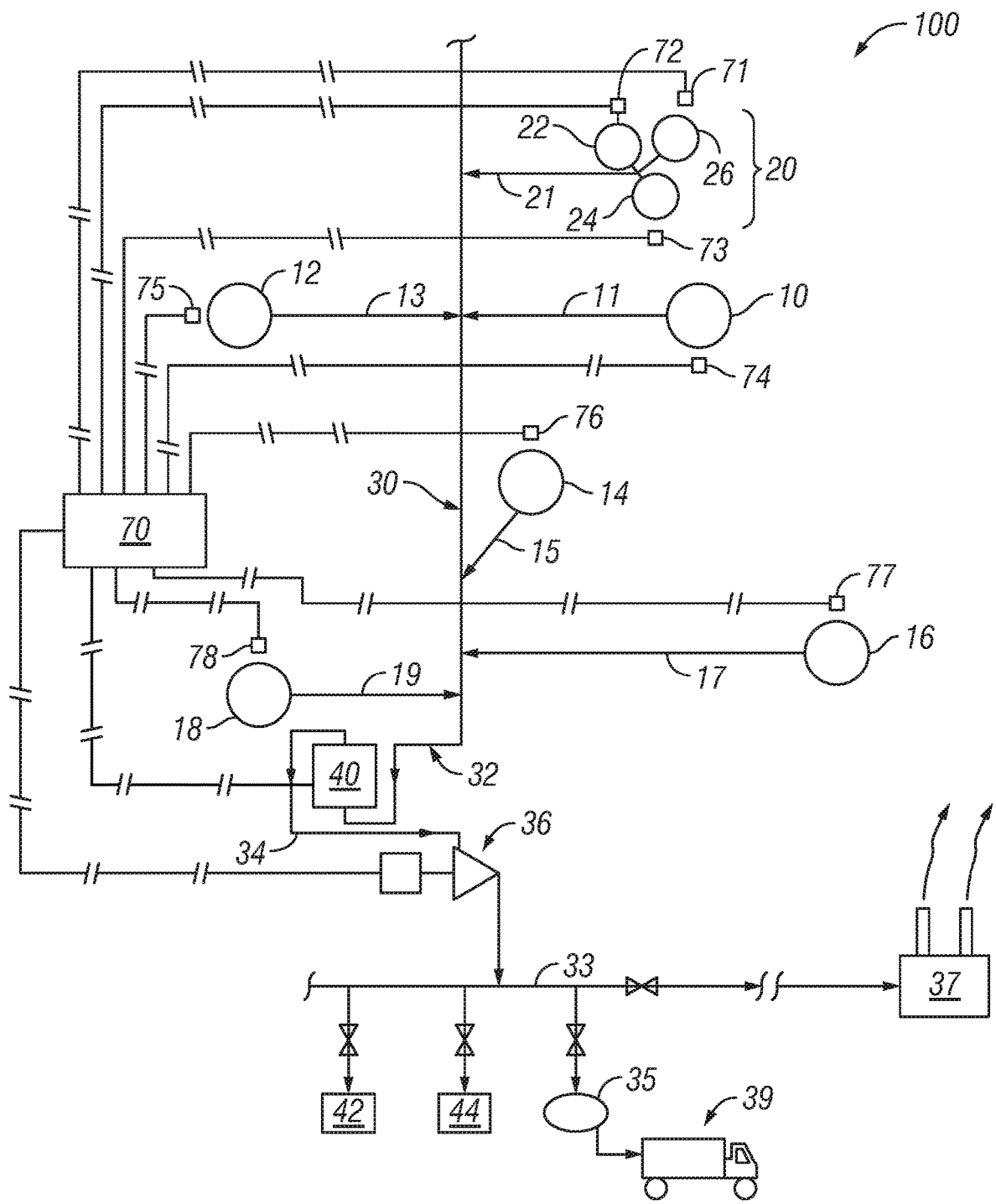
FIG. 1 is a simplified schematic overview illustration of an exemplary embodiment of the system for aggregating and processing of biogas to electrical generation and/or to methane, according to the invention.

The following non-limiting detailed descriptions of examples of embodiments of the invention may refer to appended Figure drawings and are not limited to the drawings, which are merely presented for enhancing explanations of features of the technology. In addition, the detailed descriptions may refer to particular terms of art, some of which are defined herein, as appropriate and necessary for clarity.

In the specification and claims, the term "remote," as it pertains to the geographic location of biogas sources that are linked by the network of conduits to a portion of the network (a common biogas header pipe) that conveys and feeds biogas to the central treatment/processing facility, means that the biogas sources are geographically distant from each other (i.e. not located on the same farm, or waste disposal site, for example). Absent the network of conduits, the biogas supply from these sources would have been processed separately at each of the biogas sources, if at all.

A "biogas source," as the term is used in the specification and claims, means a source of biogas such as, but not limited to, an organic waste digester that digests animal waste (e.g. manure from a dairy or a waste disposal site) or a landfill, for example, and may include several digesters/landfills at the same geographic location that are linked together and may be counted as a single remote biogas source. The term "biogas" means a gas containing methane that originates from animal waste or landfills. Biogas contains several components such a hydrogen sulfide and carbon dioxide, aside from methane. When purified to standards of methane concentration suitable for injection into pipelines, it is referred to as biomethane.

A remote location may include a biogas conditioning plant that not only removes hydrogen sulfide and water but also removes carbon dioxide thus reducing the quantity of gas that is needed to be collected and transported to the generators and/or to the centralized upgrading plant. This could be a membrane-based biogas conditioning package that selectively separates methane form $H_2O$, $H_2S$ and $CO_2$. In an exemplary embodiment, the centralized upgrading plant could receive biomethane (as opposed to biogas) and thus its primary purpose would be, under control of the central processor to accept this feed gas, remove any residual contaminants in order to meet pertinent applicable utility specifications, and then compressing and injecting the purified biomethane into the pipeline.

A networked collection system may also include a portion of the system where the biogas or biomethane is conveyed from the remote source location to the centralized location, or generators, via tank cars. The transported biogas may be off loaded at the centralized treatment plant for purification, quality control and delivery into the pipeline. The control and reporting of this "virtual" pipeline would also provide data to the central controller so that the entire system is coordinated and controlled.

In general, the processing of biogas to biomethane at each location where biogas is produced means that equipment and labor has to be expended at each location. Often, this is not economically feasible. According to exemplary embodiments of the invention, biogas from a geographically widely spread out plurality of biogas sources can be accumulated in a network of conduits (pipelines), often linked into a common header pipe, and carried in these conduits to a central gas treatment/processing facility. In addition, in order to deliver the produced biomethane (RNG) it is necessary to bring it to a centralized location where the local gas utility is ready willing and able to receive the gas into their natural gas distribution or transmission system for delivery downstream to customers. This minimizes the outlay of capital in equipment but increases the cost of the conduits. However, advantageously, these conduits may be of inexpensive polymer materials that are impervious to attack by chemicals found in biogas, such as water and hydrogen sulfide, which has a highly offensive odor ("rotten egg stench") and is readily detected. However, the collection, or aggregation, of the biogas from far-ranging farms, landfills and other sources and processing of the aggregated volume of biogas to biomethane presents several challenges that must be met to produce methane that is of a purity acceptable for combustion in power plants, and for use in producing CNG, while maintaining standards of safety.

In addition to the challenges of biogas aggregation, transport and processing, there is also the issue of distribution of the produced biomethane into natural gas pipelines. In general, pipelines have a system of requiring a gas supplier to contract in advance (by about 24 hours) the volume of approved quality methane it will be able to supply to the pipeline. Failure to meet the contracted supply results in penalties. Accordingly, there must be an accurate determination made in advance (about 24 to 36 hours in advance) of the amount of biogas that will be available to convert to biomethane for charging to a natural gas pipeline, and the remote sources that will supply this biogas. In addition, the biogas supply to the central treatment facility must be controlled. This presents significant challenges. While natural gas produced from a geological formation has relatively predictable rates of production or can be turned off an don as needed as it is stored in an existing geological formation, in a biogas supply system, the volume production of biogas is dependent upon many factors, including weather, ambient temperature, conditions at the waste digesters, remaining storage capacity, and the like that are not readily and accurately predictable. In addition, biogas may be routed at the remote source to a generator or fuel cell for direct conversion to electricity into the grid and/or to a PEV charging station, or to operate equipment at the remote source. Accordingly, the central controller should take into account the amount of biogas available at the remote sources (whether from manual data input or from automated measurements), and the potential alternative disposition of the biogas and address the challenge of being able to predict at least 24-36 hours in advance the availability of biogas to be charged to the treatment facility that will produce a predictable supply of biomethane.

The present technology uses data collected at each of the remote sources of the system that are able to supply biogas to assess biogas availability at each source at least about 24-36 hours in advance and uses this data to be able to commit to inject biomethane from this available biogas supply into the natural gas pipeline. The collected data is collected automatically or manually estimated at each remote source and input to the central controller.

As explained in more detail here below, in some examples the waste digesters have expandable roofs that deflect upward as gas accumulates under the roof. The deflection may be measured, by laser, for example, and the gas volume available can be estimated from the deflection. This provides a means for estimation of the total volume of biogas that could be continuously processed to biomethane and injected into a pipeline. Of course, other methods than roof deflection measurements may also be used. For example, human observation, or measurement of biogas pressure under the roof Several exemplary embodiments of systems that treat biogas to produce biomethane for natural gas pipeline injection (or other disposition as described herein) are set forth here below. As already pointed out here above, some of the biogas can be directly converted to electricity in fuel cells. And, as pointed out above, some of the biomethane may be used to make CNG. However, for the sake of simplicity, the explanations may focus mainly on biomethane for natural gas pipeline injection. There are some common technologies among the provided examples, and some variations between them as to apparatus. Nonetheless, each has in common the detection of the volume of biogas available at the remote sources either in real time or periodically. In addition, the connecting network of conduits has a biogas "hold up" volume that is also available to be processed as part of the biomethane that is contracted to be delivered. The technology presented herein provides access to remote biogas sources that are geographically widely distributed, predicts (based on instrumentation and/or human data input) the availability of biogas from these remote sources at least 24-36 hours in advance, safely aggregates the biogas via a network of conduits, and conveys the biogas to a single conversion facility to produce biomethane where it is converted to biomethane and controlledly compressed into a natural gas pipeline and/or supplied to a CNG facility, and/or used in a fuel cell to directly make electricity.

In summary, in an exemplary embodiment there is provided a biogas collection, purification and biomethane delivery system. The system aggregates biogas from a plurality of remote sources, deducts remote uses such as for generation or other biogas take-off, adds virtual deliveries and treats the biogas to produce biomethane. The system comprises: a network of conduits configured to convey biogas from the plurality of remote sources of the biogas based on a monitored or automatically detected availability of biogas at each respective remote source. A biogas compressor at each of the remote locations is controlled by a central controller that utilizes data that includes biogas availability data. The central controller is configured to instruct the biogas compressor to supply compressed biogas to several potential processes, as well as to a central biogas processing facility, depending upon input data. Thus, the biogas may be compressed to a fuel cell for direct conversion of the biogas to electricity to power at least some of the equipment at the remote source, or the electricity can be transmitted to a charging station for PEVs to charge vehicle batteries. Compressed biogas can also be supplied to a biogas header that conveys the biogas to the central processing facility. Here, the received biogas from many remote sources in the network of linked-together plurality of remote sources is treated and processed from biogas into biomethane. The central processing facility has an input compressor that is controlled by the central controller that operates based on data including the data from the remote sources about the availability of biogas at the sources. The central treatment facility includes several biogas treatment operations, including but not limited to a biogas hydrogen sulfide removal stage; an activated carbon scrubber (which may be downstream from the hydrogen sulfide removal stage); a carbon dioxide removal stage (which may be) downstream from the hydrogen sulfide removal stage for purifying the biogas into biomethane by removal of carbon dioxide. And the central processing facility also has a biomethane gas compressor for compressing the produced biomethane, also under control of the central controller. If the biogas to biomethane upgrading is handled at some or each remote location then the central treatment plant still remains as the control hub and RNG product quality station to ensure the RNG meets the utility gas specifications (e.g. Rule 30 for Sempra and Rule 21 for PG&E) Thus, the biomethane may be charged to a fuel cell for direct conversion of the biomethane to electricity to power at least some of the equipment at the treatment facility, or the electricity can be transmitted to a charging station for PEVs to charge vehicle batteries. The biomethane can also be charged to a system for compression to CNG. Or, the biomethane can be compressed to a natural gas pipeline, as explained in more detail here below. The decision (and control) of the biomethane disposition to the natural gas pipeline or to CNG or to fuel cells to create electricity for PEVs is based on several control variables including biogas availability, projected biogas availability and (use same language as previously)

In general, in a simplified explanation of an exemplary embodiment, the central processing facility has several processing units. The processing units may be skid-mounted. Among the processing units are a hydrogen sulfide removal stage, which may include, but is not limited to, a sodium hydroxide scrubber or iron sponge columns. Further, an activated carbon scrubber is deployed downstream from the hydrogen sulfide removal stage to remove further residual amounts of hydrogen sulfide and other contaminants susceptible to activated carbon removal. To remove water vapor, a drier may be located downstream from the activated carbon scrubber. At this stage, the biogas still has significant amounts of carbon dioxide. Thus, a carbon dioxide removal stage, which may include, but is not limited to, a membrane separator that separates out the biomethane from the carbon dioxide, which may be vented. There may be a gas chiller downstream from the carbon dioxide removal stage to chill the biomethane which is at this point high purity combustible methane. A system compressor is configured to compress the biomethane at a controlled rate of compression that is based on data that may include data received from the instruments measuring biogas accumulation at biogas remote sources in the network, but that is also based on the amount of gas being metered into the pipeline. The gas hold-up in the conduit network of the system may also be used as part of the control data for the compressor.

FIG. 1 is a simplified flow diagram depicting an overview of process flows of an example of a system for aggregating and processing of biogas to methane, according to the invention. The illustrated system 100 includes a plurality of remote biogas sources 10, 12. 14, 16, 18, and 20. The remote biogas source 20 includes, in the example three digesters (but more or fewer are envisaged) are illustrated, as biogas sources 22, 24, and 26 that not remote from each other (i.e. they might be on the same farm if these are animal waste digesters) but that are remote as a group from the other illustrated biogas sources 10, 12, 14, 16, and 18. Thus, remote biogas source 20 that includes biogas sources 22, 24 and 26 is a remote biogas source, as that term is used herein. The remote biogas sources each deliver biogas into a network of gas aggregation conduits. In this example, for instance, remote biogas source 10 delivers to conduit 11, remote biogas source 12 delivers to conduit 13, remote biogas source 14 delivers to conduit 15, remote biogas source 16 delivers to conduit 17, remote biogas source 18 delivers to conduit 18, and remote biogas source 20 delivers to conduit 21. Each of these conduits in turn feed biogas to a conduit 30 that ultimately connects to a main feeder conduit ("header") 32, which is a portion of the network of conduits, and that delivers the accumulated biogas to the central processing facility 40. Processed gas (methane of combustible purity) that exits the central processing facility 40 in conduit 34, is compressed in a system compressor 36 either into a pipeline 33 for delivery to a power plant 37 for combustion, or to storage 35, and/or to tank cars 39 to deliver. The biomethane may also be routed to processing to CNG 42. Moreover, the biomethane may also be charged to a fuel cell 44 for direct conversion to electricity.

The remote biogas sources may not be of uniform size and are generally not producing biogas at the same rates. Accordingly, with biogas availability being variable within the system, controls are needed so that the system can operate continuously with reasonable predictability of biomethane supply capability, as far as possible based on the availability and expected availability of biogas from the sources. Of course, even if all biogas supply from the biogas sources were shut in, there is still an amount of biogas held up in the volume of the conduits, and in the volumes within the central processing facility that could be available to process biomethane. Depending upon the rate of compression of gas, this gas hold-up in the system represents a "time-lag" within the system that a controller can take into account.

In the exemplary, simplified overview illustration of FIG. 1, the controller 70 receives data from each of the remote biogas sources relating to biogas available to enter the network of conduits. Of course, in some systems not all biogas sources will have such capability, and at least some may lack the measuring instruments to detect and transmit data about biogas availability. In the illustrated example, the central controller 70 receives input data about biogas availability from detector/transmitters 71, 72, 73, 74, 75, 76, and 78 (or from human input based on observations at these remote sources). The central controller 70 is configured to process this data to control the rate of gas compression at a biogas compressor at each remote source (not shown in FIG. 1; shown in FIG. 2 as compressor 220 at each exemplary remote source), and control the biogas feed compressor (not shown in FIG. 1, but shown in FIG. 3 as compressor 45) at the treatment facility 40, as well as the biomethane gas compressor 36. By suitably controlling the rates of compression taking into account the volume of predicted available gas at each source, a predictable and relatively steady rate of gas delivery can be achieved from the system to the natural gas pipeline. Of course, if a portion of available biogas is being routed to a fuel cell at a remote source, the central controller has to take into account that this biogas is not available to the central biogas treatment facility.

Biomethane gas to the natural gas pipeline upgrader must be at acceptable purity and quality (H2S, O2, inerts, water, etc.). The utility operator requires delivery into its point of interconnect (POI) at a flow rate between the minimum and the maximum rates as described in an interconnection agreement so that thee revenue metering equipment can remain within calibration. This min/max flow must be uniform and must be communicated to the utility prior to delivery including a duration of flow.

Figure 2:
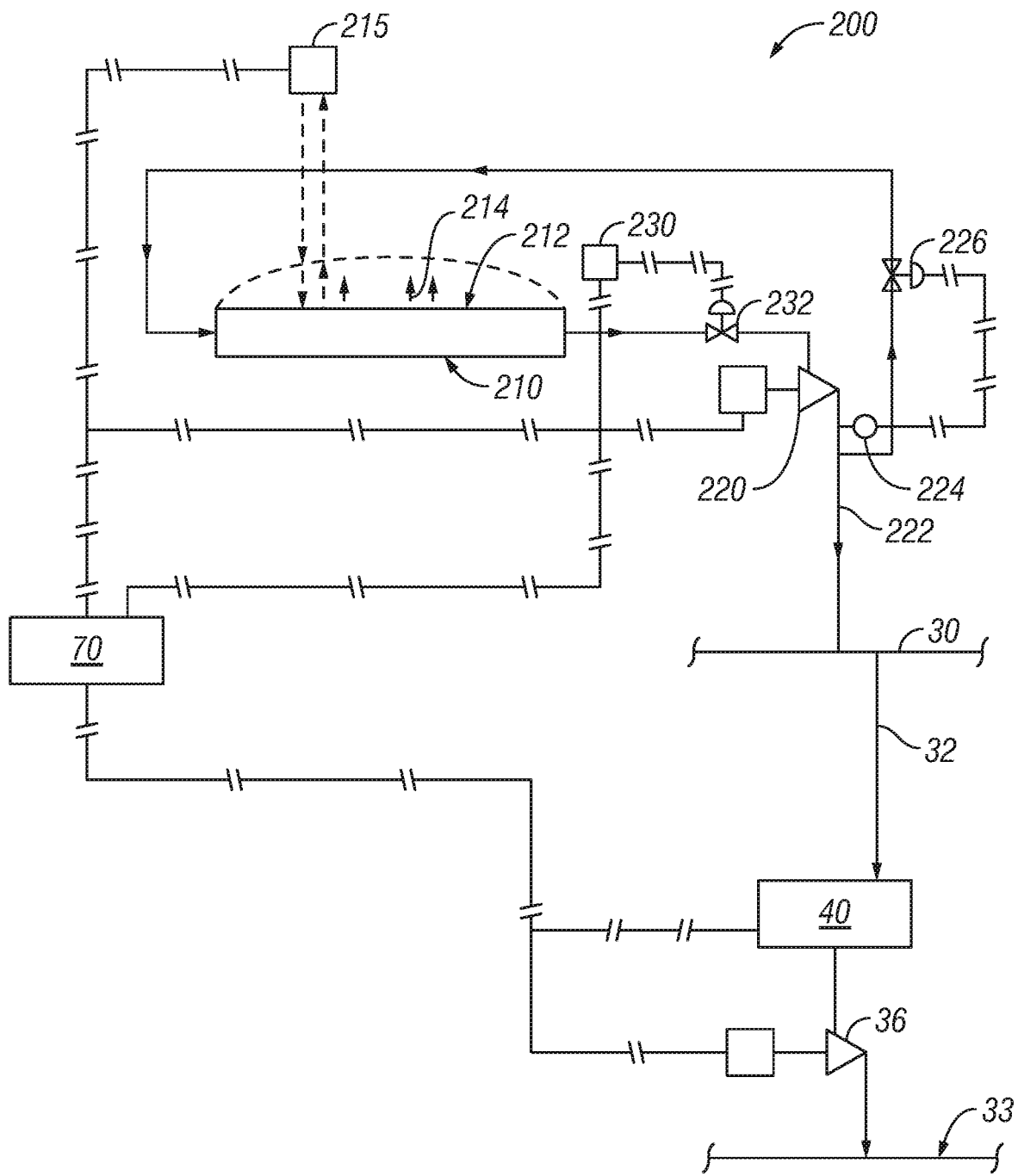
FIG. 2 is a simplified schematic illustration of an exemplary embodiment of the processing system converting biogas to methane, according to the invention.

FIG. 2 is another schematic simplified overview flow diagram, not to scale, of an example of a remote biogas source 200 that includes a digester 210 that produces biogas, and that has a flexible expandable roof 212, sealed in an airtight seal to the digester. Thus, produced biogas 214 accumulates under the roof gradually causing the roof 212 to expand upward from a first flat shape (shown in dark line), to an expanded state billowed out upwards by biogas, as shown in dashed lines. An instrument, such as, but not limited to, a laser deflector measuring device 215 can be used to detect the degree of deflection of the roof 212 and transmit this data to the central controller 70 (see also FIG. 1). Based on this transmitted data, the central controller 70 can control a rate of the local biogas compressor 220. The local compressor 220 compresses biogas into the network conduit 30, as in FIG. 1, via a connecting conduit 222. Network conduit 30 conveys the biogas to the conduit 32 that feeds biogas to the central processing facility 40. As explained with regard to FIG. 1, processed gas (biomethane) from the central processing facility 40 is charged to the system processed gas compressor 36, and thence to pipeline 33, under control of central controller 70.

In an exemplary embodiment, the flow rate from the local biogas compressor 220 is measured by flow detector 224, which controls a control valve 226. This allows the recycling of a proportion of the biogas back into the digester through valve 226, which can have the benefit of reducing the hydrogen sulfide concentration in the biogas. In general, an amount of recycle of from about 2 to about 8 percent by measured volume of biogas can be helpful in this regard.

A hydrogen sulfide detector 230, or several of these, may be located in the vicinity of the digester 210 and in the vicinity of the network pipelines. When the detected level in the atmosphere increases above a preset threshold, the detector shuts down the cutoff valve 232 thereby preventing further flow of the gas through any leak that might have arisen. In addition, a signal may be sent to the central controller 70 to indicate an alarm condition and initiate appropriate action.

Figure 3:
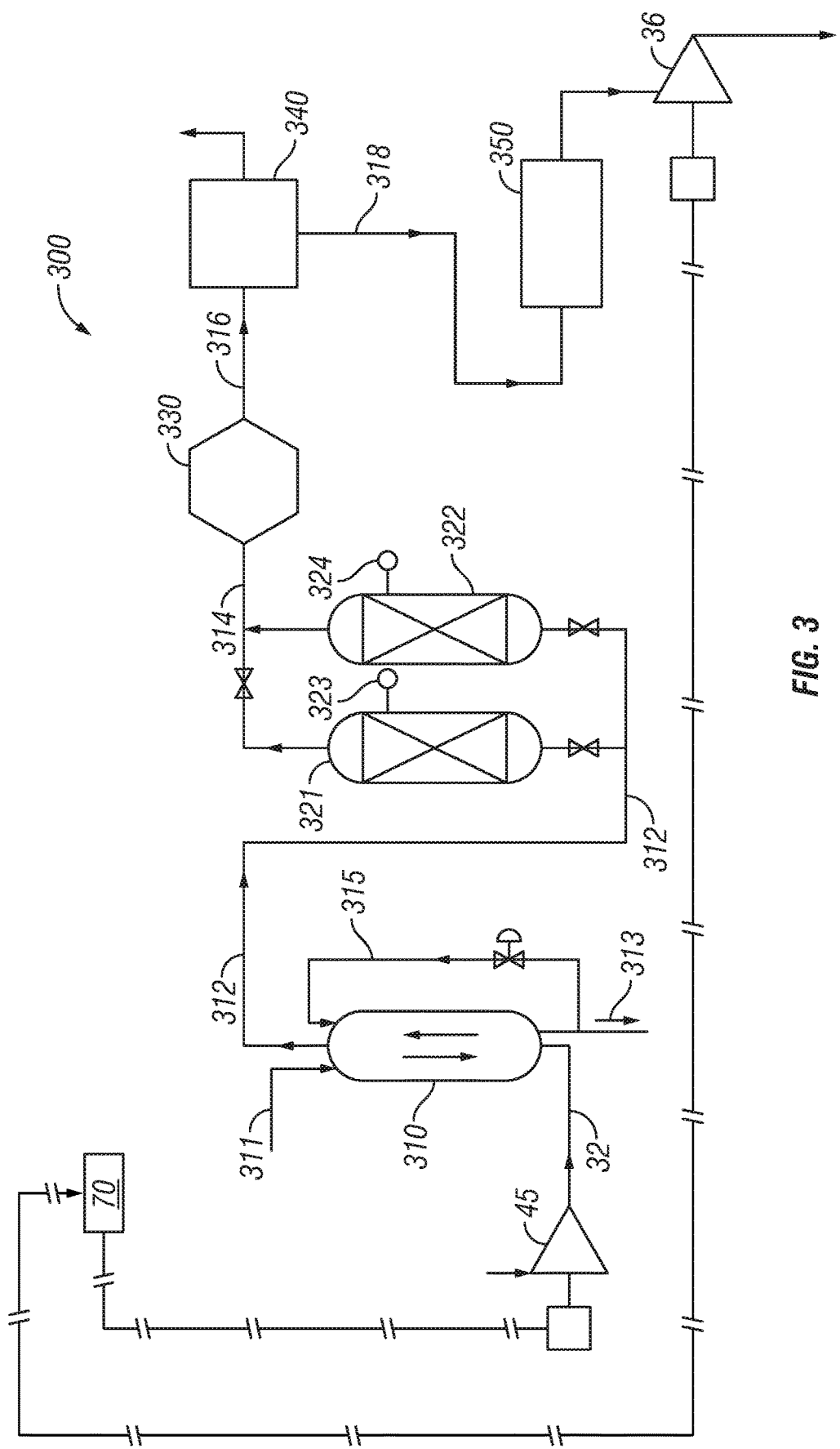
FIG. 3 is a simplified schematic illustration of an exemplary biogas source that may be a part of the system for aggregating and processing of biogas to methane, according to the invention.

FIG. 3 is a schematic overview of a flow diagram, not to scale, depicting process flows of an example of a central processing system 300 that upgrades biogas to methane grade gas. Biogas from the plurality of remote biogas sources enters the processing facility in conduit 32. This conduit feeds the raw incoming biogas to the hydrogen sulfide removal stage 310. In the exemplary embodiment, this includes a scrubber in which a solution of sodium hydroxide in water is contacted, preferably in counter-current flow, with the raw biogas charged to the scrubber. As illustrated in the example, sodium hydroxide solution 311 enters at the top of the scrubber 310 flowing downward, while the biogas enters at the base in 32 flowing upward. A portion of the sodium hydroxide solution is removed from the bottom in conduit 313, a portion is recycled in conduit 315, and the scrubbed biogas leaves the top of the scrubber in conduit 312. After this scrubbing stage the hydrogen sulfide content of the biogas is significantly reduced but might not yet meet combustion standards.

For further biogas purification to meet combustion standards, the gas is charged to an activated carbon gas purifying unit that removes residual hydrogen sulfide such that the purified biomethane meets standards for combustion, as to residual hydrogen sulfide. As illustrated in the example, a pair of activated carbon columns 321, 322 are used in tandem so that one is in use, while the other is being regenerated or refilled, as the activated carbon becomes spent. The packed columns may be equipped with sensors 323, 324 to detect hydrogen sulfide breakthrough in the packed beds to facilitate the switchover from one packed bed to the other and maintain treated gas quality as the biogas exit in conduit 314.

After the gas has been purified to remove hydrogen sulfide, the gas may contain moisture. Thus, the purified biogas is now charged to a dryer 330 where residual moisture is removed. Gas drying may be achieved with a desiccant packed into the dryer, or by other means. The dried gas in conduit 314 is charged to a carbon dioxide removal unit 340. A non-limiting example of such a unit is a membrane gas separator, where the membrane is selected to separate the methane gas in the purified biogas from the much larger carbon dioxide molecules also present in biogas. The methane-rich gas exiting from this unit 340 in conduit 318 has significantly reduced carbon dioxide content and is then routed to a chiller 350 for cooling prior to controlled compression in the system biomethane compressor 36 into a natural gas pipeline.

Summarizing, there is provided an exemplary method of aggregating and treating biogas from a plurality of remote sources to convert the biogas to a processed combustible biomethane gas for compression to a natural gas pipeline, or storage or processing to CNG or conversion to electricity via a fuel cell. The method includes the steps of detecting the availability of biogas at remote sources to permit prediction of biogas availability about 24-36 hours in advance, coupling the plurality of remote biogas sources to a network of conduits and delivering the biogas from the remote sources to a central processing facility. Treating the delivered gas by removing hydrogen sulfide in the biogas at the central processing facility. The treatment may include contacting, in counter-current flow, with a solution of sodium hydroxide to react with the hydrogen sulfide. The method further includes removing trace residual hydrogen sulfide and other contaminants by flowing the gas through activated carbon packed beds. The treated gas is charged to a membrane separator to separate out carbon dioxide from the desired biomethane in the biogas.

Other exemplary method steps may include measuring or observing a deflection of flexible roofs of remote sources and using the deflection measurements or input observations via a central controller configured to control the individual biogas compressors at the remote sources, the biogas charge compressor at the central treatment facility and the processed gas compressor. Further, the methods may include measuring hydrogen sulfide concentration in the atmospheric environment at the remote biogas sources and along the network of conduits and using the measured concentration to control cut-off valves when a predetermined concentration is detected indicating a leak.

Figure 4:
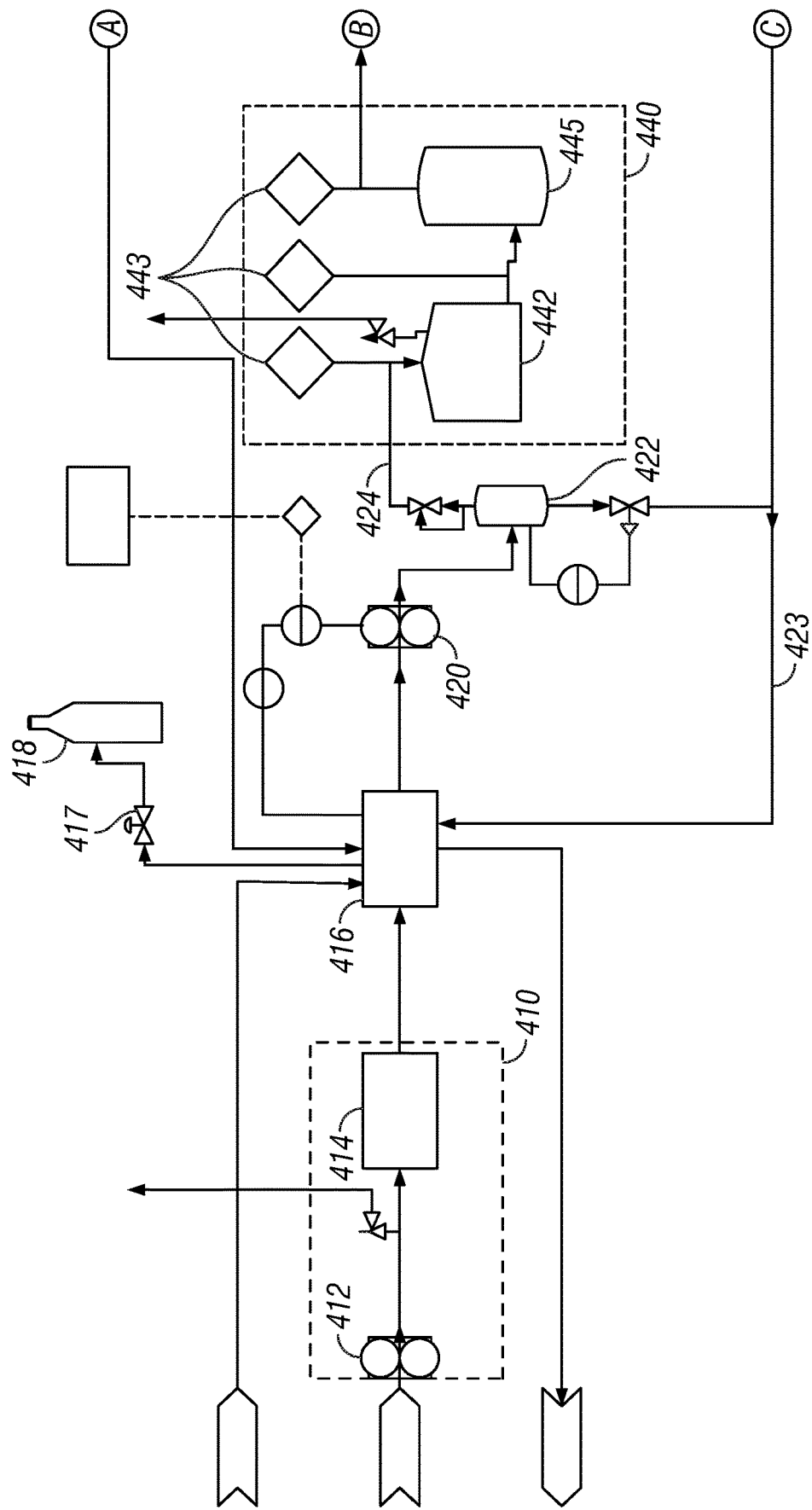
FIG. 4 is an illustrative simplified process flow diagram of an exemplary embodiment of a biogas processing facility at a remote source.
Figure 5:
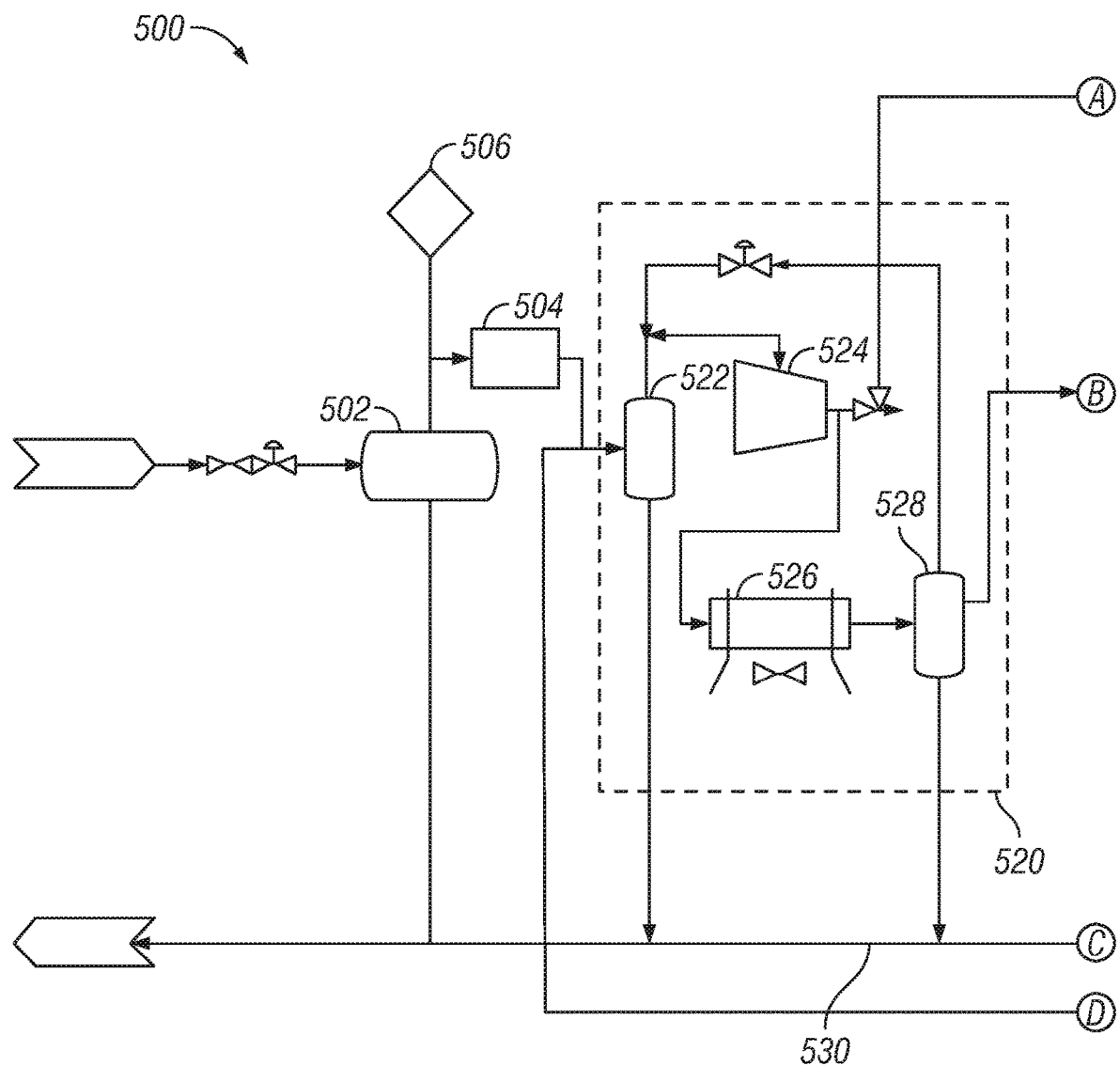
FIG. 5 is an illustrative simplified process flow diagram of an exemplary embodiment of a central facility processing biogas from a plurality of biogas remote sources to biomethane.
Figure 5:
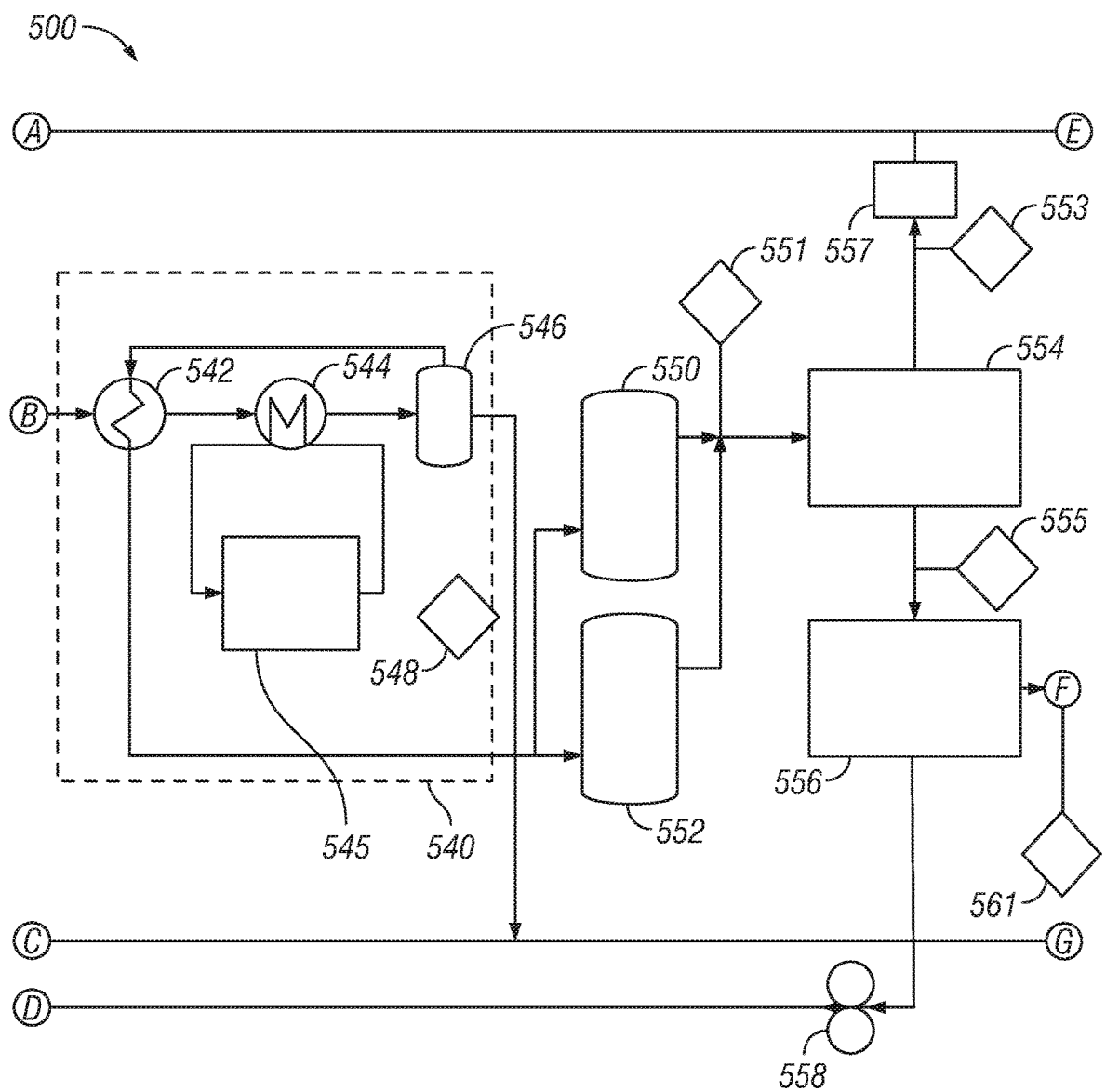
Figure 5:
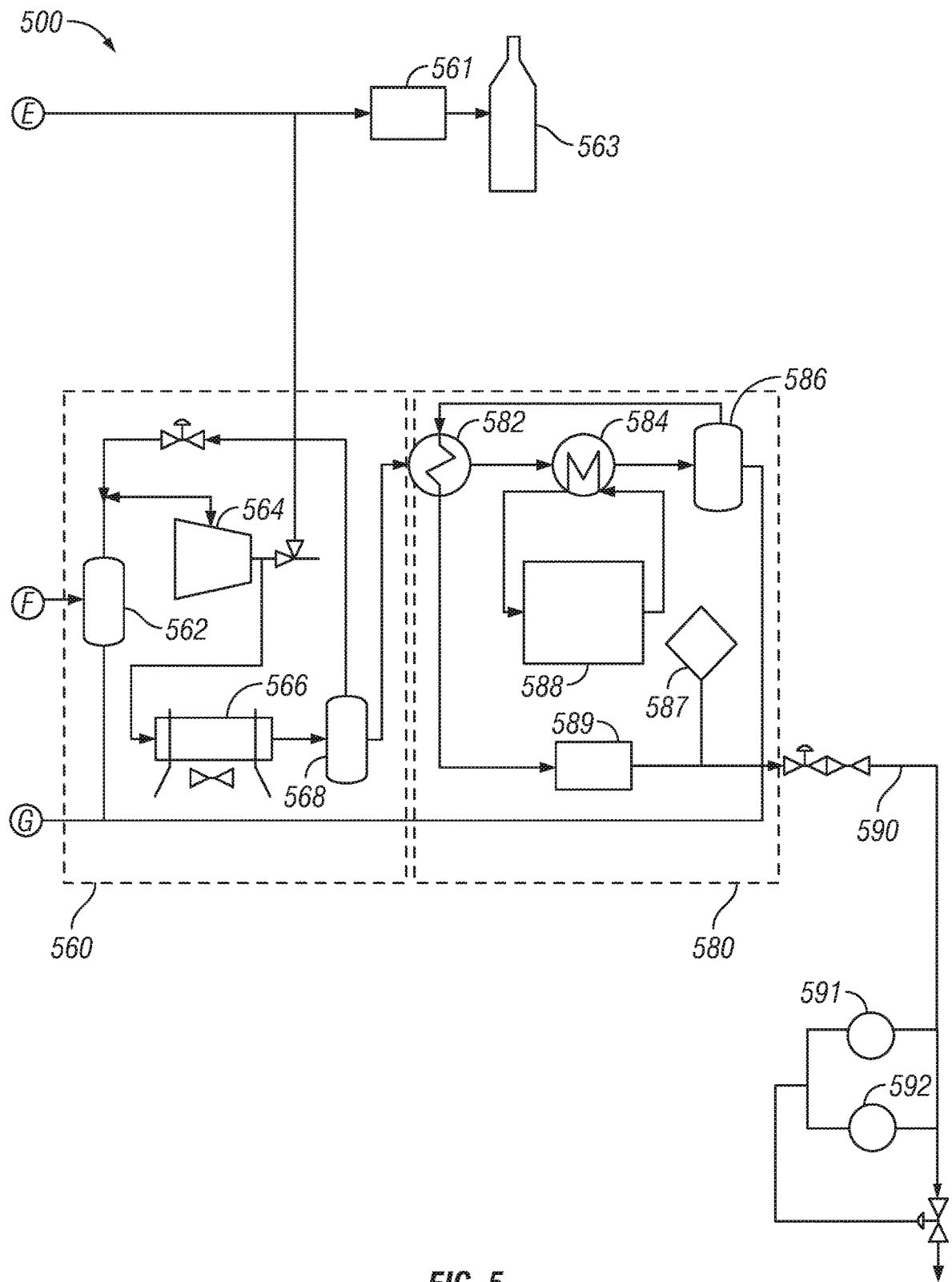

The exemplary process flow diagrams of FIGS. 4 and 5 also illustrate details of the processing of biogas from digesters, converting animal waste to biogas, to biomethane (meeting combustibility specifications set by regulations in the various states), and illustrate variations from the foregoing examples of overview process flow diagrams. Of course, the biogas may also be charged to fuel cells, as noted above, at the remote sources or at the central location or anywhere in between where access to the biogas gathering/collection line is made available. And, the biomethane produced may also be used to manufacture CNG or to produce electricity via fuel cells. Descriptions of certain ancillary equipment previously discussed will not be repeated, but can be assumed to be present as appropriate. FIG. 4 illustrates an exemplary simplified biogas conditioning process flow chart, and FIG. 5 illustrates an exemplary simplified process flowchart for conversion of biogas to biomethane meeting regulatory standards for injection into a natural gas pipeline. In the exemplary embodiments, both FIGS. 4 and 5 illustrate the use of "skid-mounted apparatus." Of course, other non-skid-mounted equipment might also be used.

As to FIG. 4, in the illustrated exemplary process flow diagram 400, the apparatus is located near the remote biogas source, such as on a dairy farm, for example and are located on four skid platforms: 410, 440, 460 and 480. In the first skid, the oxygen generator skid 410, air enters a compressor 412 and is charged to an oxygen generator unit 414. This oxygen, together with animal waste (manure in the case of a dairy farm) charged to a digester 416 where the waste is digested under conditions that generate methane gas—biogas. Biogas from the digester is drawn under controlled conditions into the suction of a blower 420 and charged to a condensate separator for removing condensate (water) carried in the biogas. The condensate is recycled to the digester or to a sump 416. The biogas exits from the top of the separator 422 and is charged to the apparatus on skid 440 that perform the function of hydrogen sulfide (H2S) removal from the biogas. In the illustrated example, the biogas is charged first to an iron sponge 442 that removes a large proportion of the hydrogen sulfide. The removal process is monitored by H2S gas analyzers 443. The biogas then enters an activated carbon column 445 where further amounts of H2S are removed. The biogas exiting from the activated carbon column 445 desirably has a level of H2S concentration that is within limits regarded as safe for transportation in a pipeline. The cleaned biogas then enters the compressor system mounted to the compressor skid 460. The biogas passes into a compressor suction gas scrubber 462 where water is removed and drained under control to the recycle water system conduit. The biogas is compressed in the compressor 464, and the compressed biogas is cooled in the compressor cooler 466. The cooled, compressed biogas then flows through a compressor discharge scrubber for further moisture removal. The removed water is routed to the water recycle conduit and the compressed biogas is charged to a dehydration system mounted to skid 480. The compressed biogas enters a first gas/gas pre-cooler heat exchanger 482 where cooled compressed biogas is used to cool the incoming warmer compressed biogas. The compressed biogas is cooled to some extent in this pre-cooler than enters into a water-cooled heat exchanger 484 where chilled water from a water chiller 486 further cools the biogas to the range of about 40° F., for example. The chilled biogas then enters a chiller separator to remove any condensed water in the gas for recycle. The chilled biogas flows to the pre-cooler 482 to cool incoming biogas. Upon exiting from the pre-cooler, the now warmed biogas flows through a gas meter 490. The biogas is then either charged to a truck for transportation, or to a pipeline to convey the biogas to a gas processing facility 500, as illustrated in exemplary form, in FIG. 5.

FIG. 5 illustrates an example of a process for treating biogas to convert it to biomethane that meets regulatory standards for feeding the gas into natural gas pipelines for subsequent use in power generation, commercial use, and residential use. The process equipment may receive incoming biogas from several biogas producing facilities, for example like that illustrated in FIG. 4. The process 500 shows apparatus mounted on four skids: 520, 540, 560 and 580. Biogas from a process such as that illustrated in FIG. 4 enters a filter/separator 502, optionally mounted to skid 520. The liquid water separated from the biogas is routed in water recycle conduit 530 for reuse. The filtered off gas is analyzed 506, and the volume is measured 504 before being charged to a compressor suction scrubber where water is removed from the biogas for recycling. The scrubbed biogas is compressed in the compressor 524, and the compressed biogas is cooled in the compressor cooler 526. The exiting cooled compressed biogas enters a compressor discharge scrubber 528 where condensate water is removed for recycling. The biogas flows to a gas/gas precooler 542 on skid 540 where it is pre-cooled against colder biogas, and thence to a chilled water cooler 544 where the biogas is further cooled. The cooled biogas is then charged to a chiller separator 546 from which cold exiting biogas is routed to the pre-cooler 542 to cool the incoming biogas, and from which condensate water is routed to recycling. The cold biogas is analyzed 548 and routed to a pair of tandem operating activated carbon filter columns 550, 552 to remove residual impurities in the biogas. The purified biogas exiting the activated carbon treatment is analyzed 551 and charged to a series of membrane separators to remove carbon dioxide and thereby increase the concentration of methane in the biogas. Carbon dioxide rich gas exiting from the membrane first stage 554 is analyzed 553, metered 557, and vented via a stack 563. Methane-rich biogas exiting the first stage 554 is also analyzed 555 and flows into a second stage of membrane separation 556. One portion of the exiting methane gas that includes carbon dioxide is routed to the blower 558 and recycled back to the compressor suction scrubber 522 so that the biomethane in the gas stream is not lost but is recycled to be reprocessed and enriched in methane content. The other portion of the methane-rich biogas from the second stage 556 is charged to the biomethane compression skid 560.

By recycling a selected appropriate portion of the methane-rich biogas from the second stage membrane 556, the concentration of methane in the system upstream from the membrane stages 554, 556 is increased and the concentration in the gas exiting the membrane separation step is increased. Clearly, the higher the proportion recycled, the higher the methane concentration at the exit of the separation stages 554, 556 will be. Thus, the amount of recycle is set to a level that ensures the exiting biomethane for compression to the natural gas pipeline meets specifications.

Methane-rich biogas exiting the second stage separator 556 is analyzed 561, and gas meeting methane specifications (hereafter biomethane) is charged to a compressor system mounted on skid 560. The compressor system includes a compressor suction scrubber 562 to remove water from the biomethane and route the water to recycling. The biomethane is then charged to compressor 564 and the exiting compressed biomethane is cooled in a compressor cooler 566. The cooled biomethane is charged to a compressor discharge scrubber to remove condensed water for recycling, and the biomethane is charged to a chiller skid 580 that includes further gas cooling apparatus. The biomethane enters a gas/gas precooler 582 where it is cooled against chilled biomethane. Then, the pre-cooled biomethane enters a water-cooled exchanger 584 where it is further cooled (to around 40° F.) against cold water from water chiller 588. Any separated condensate is separated out in the chiller separator 586 and routed to recycle. The chilled biomethane is routed to the pre-cooler 582 to cool incoming biomethane. The warmed biomethane then flows through a gas analyzer 587 and a gas meter 589 and can then be routed at 590 to a gas pipeline or other transport means. Gas analyzers and gas flow meters at each remote location measure and provide data to the central controller. The central controller receives as inputs variables including but not limited to pressures, gas analyses, humidity, oxygen %, inert %, H2S ppm, data about the presence of other contaminants (e.g. siloxanes for waste water and landfills), and the like that are or become necessary under particular circumstances to control the entire system.

As pointed out here above, the treated biogas, now meeting natural gas specifications, can be used in power plants as fuel, and can also be used as a substitute for fossil-fuel methane in production of CNG for transport fuel. It can also be charged to fuel cells and converted directly to electricity. The overall effect of the systems proposed herein is to reduce greenhouse gas emissions.

In another exemplary system and apparatus, the biogas produced by the plurality of digesters and collected from the remote digesters, as described above, and treated is treated locally, on or near the dairy farm for example, to remove the bulk of the hydrogen sulfide (H2S) in the gas, and to remove moisture. This biogas having about 60% methane content and Carbon dioxide (CO2) along with residual H2S and other sulfurous compounds, is further treated in a biogas purification system in order to produce a biogas that is suitable as feedstock to a fuel cell for generation of electricity. The biogas purification system removes sulfurous compounds from the treated biogas, such as carbonyl sulfide, that are fuel cell poisons. In the case of dairy manure, the produced biogas is free of siloxanes, that are often found in landfill-sourced biogas. Siloxanes, if present, must also be removed. The biogas purification system removes sulfurous compound so that the treated biogas is "substantially free of sulfur," meaning that any traces of residual sulfur do not have a deleterious effect on the operation and cycle life of the fuel cell. Depending upon a range of factors, including the specific type of solid oxide fuel cell, sulfur (total) at less than about 1.5 ppmv or 1.6 ppmv (peak) is desirable. Fuel cells are more sensitive to COS where less than 1 ppmv is generally necessary.

Figure 6:
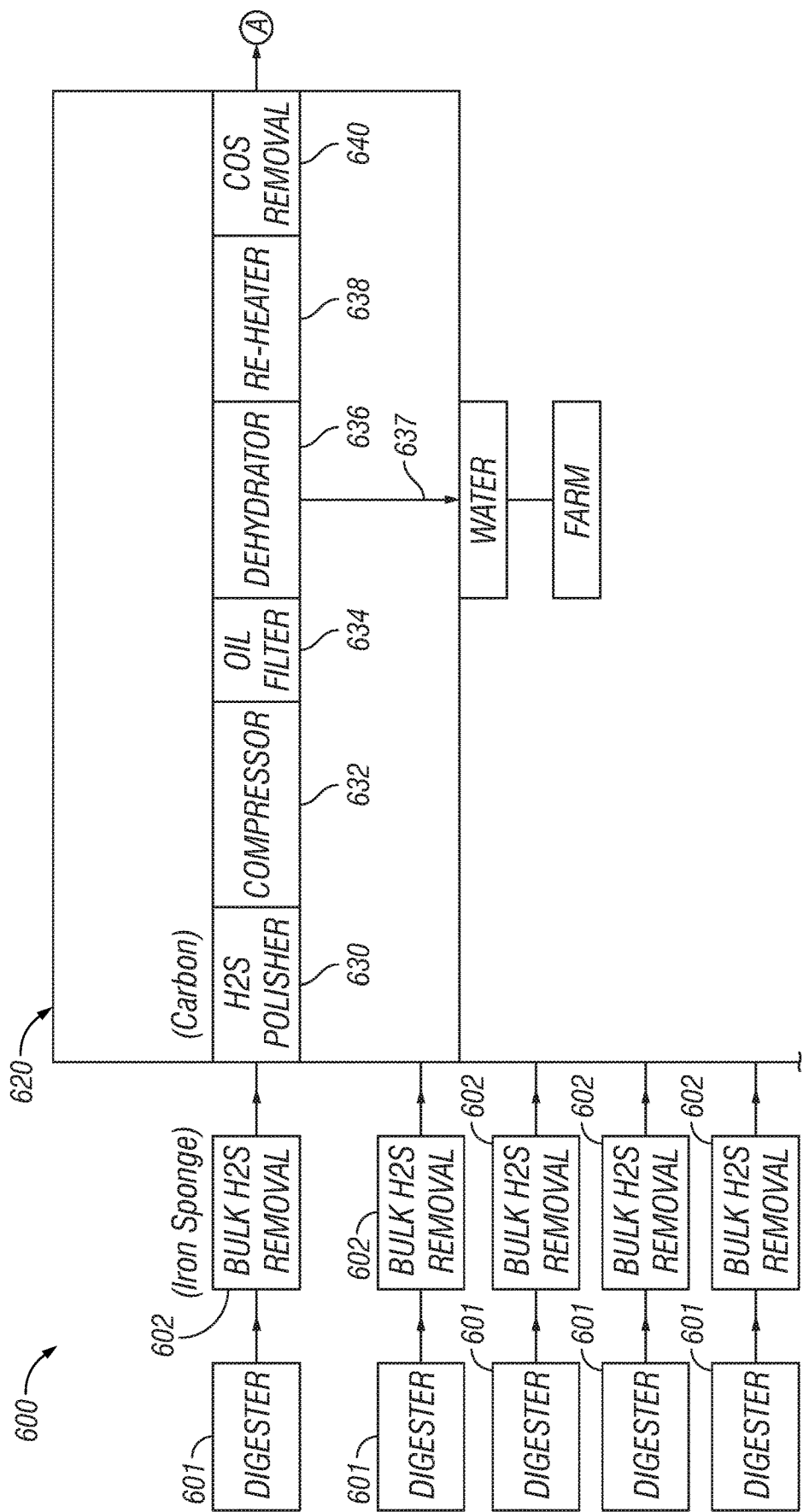
FIG. 6 is an illustrative block diagram flow chart showing an exemplary overview of a process that includes fuel cells.
Figure 6:
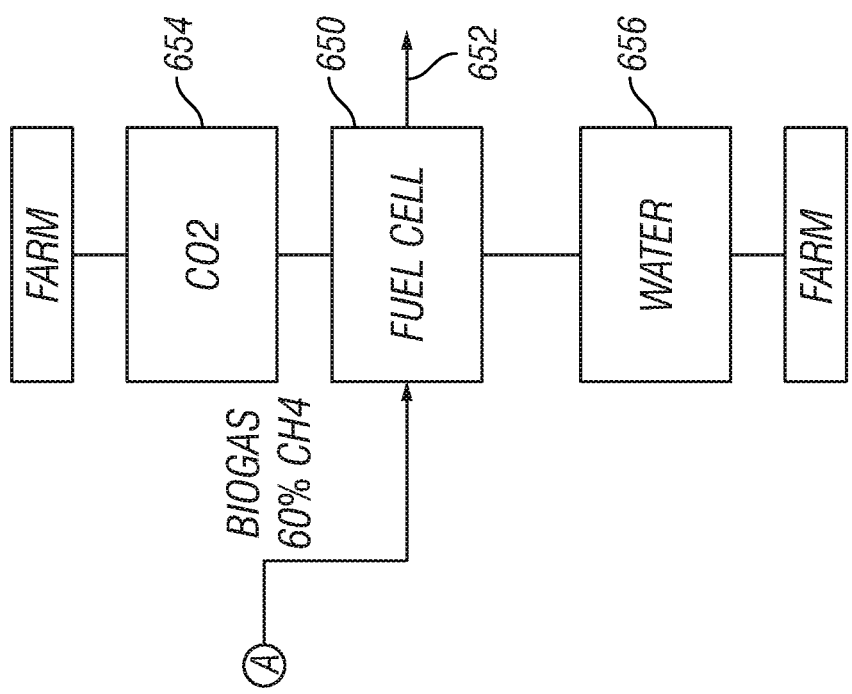

FIG. 6 is a simplified block diagram showing the flow chart of system 600 for generation of electricity from purified biogas using fuel cells in overview. Raw biogas from a plurality of waste digesters (or digester clusters), exemplified by 601, is charged to the local area biogas treaters 602 essentially to remove the bulk of the H2S, water vapor and any entrained water. Other contaminants may also be removed, as discussed elsewhere herein, if necessary. The treated biogas exiting the bulk H2S treatment facilities 602 flows at a relatively steady rate due to the digester configurations described elsewhere herein. Treated biogas exiting the local processing facilities 602 may be charged to a biogas header that transports the biogas as feedstock to the biogas purification apparatus 620, which may be skid-mounted, for convenience. The purpose of this apparatus 620 is to further purify the biogas by removing compounds that may be deleterious to the fuel cell 640; and if necessary, to further maintain the biogas flow rate above the fuel cell minimum turndown rate so that the fuel cell 640 operates continuously.

The apparatus 620 has the following operations in series: a biogas "polisher" 630 for removal of residual H2S; a compression apparatus 632; an oil filter 634 for removal of any oil that may have entered the biogas stream through the compression or other operating processes; a dehydration step 636 that removes water and moisture from the biogas and directs the water to a collector 637 for re-use on the farm (for example in the waste lagoons); a re-heater 638 that heats the biogas (which was chilled for dehumidification); and a treatment process that removes COS and H2S residue from the biogas such that the biogas can be charged to the fuel cell 650. The fuel cell produces electricity 652, and CO2 (654) that may be directed to the farm for use in plant photosynthesis, and water (656) that is redirected to the farm for suitable use.

Aside from the removal of sulfurous compounds and other possible deleterious compounds from the biogas, oil removal is required to remove any fine mist of droplets of oil that during enter the biogas and may originate from equipment and this oil may subsequently have a deleterious effect on fuel cell performance and/or life.

Fuel cell 650 receives a substantially purified biogas stream, that has been much purified compared to the biogas exiting from the local processing facilities 602. The fuel cell 650 may be, without limitation, a solid oxide fuel cell, or any other type capable of generating electricity directly from methane, with limited waste products, such as water and carbon dioxide.

The electricity from the fuel cell 650 may be utilized in any of several ways, for example including but not limited to being sent to the grid, directed to an EV charging facility, whether for private cars or government/municipal use, and at least some of it might be directed to power the system as a whole, or a portion of it.

There are advantages to sending the electrical power to an EV charging facility based in the renewable energy credits that can be obtained in some states of the United States. The biogas-sourced electricity can be readily measured as it is used to charge EV batteries, the amount of energy for each battery pack can be tracked and accumulated in a cloud-based database. This information can be used to calculate renewable energy credits (RECs) and how to apportion these between biogas electricity supplier and biogas electrical energy consumer.

Figure 7:
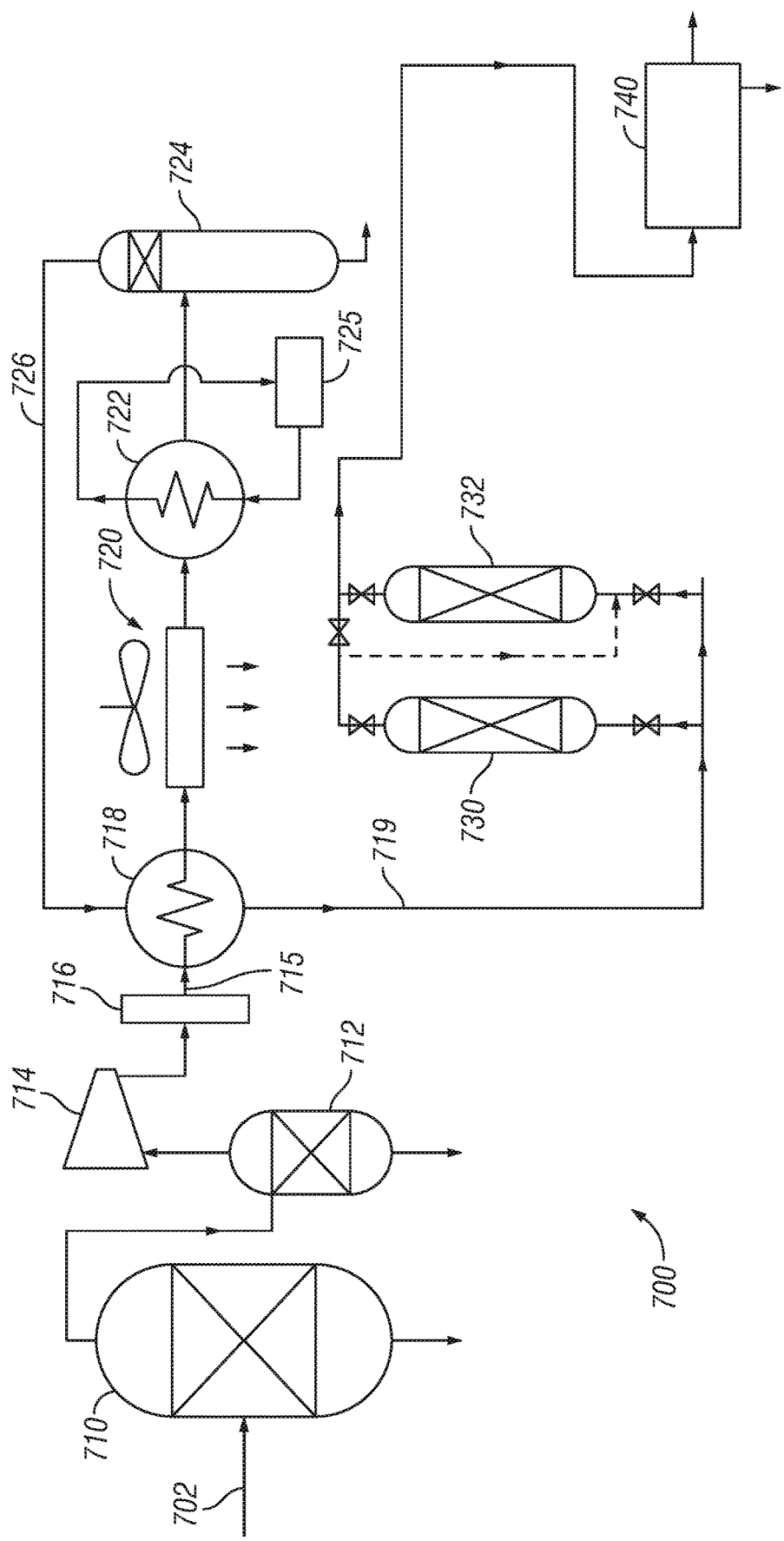
FIG. 7 is an illustrative perspective view of an exemplary embodiment of a skid-mounted biogas treatment process that receives charge of biogas, after initial bulk hydrogen sulfide removal, and provides a polished, treated biogas to a fuel cell for generation of electricity.

FIG. 7 is a simplified flow diagram of an exemplary system for biogas purification to directly provide a feedstock biogas suited to a fuel cell to generate electricity. As illustrated, an incoming already-treated biogas stream 702, that has a lower H2S content as compared to raw biogas, is charged to a treatment column 710 that is packed with a composition to remove H2S from the biogas. This packing may include, for example and without limitation, iron-impregnated wood chips or an iron sponge, as used at the local bulk H2S removal facilities 602 (See, FIG. 6). The column also provides a holdup volume sufficient to slow the gas flow rate and allow entrained water and any other liquid to coalesce and drop out of the biogas to the bottom of the column 710 for routing to a sump, for reuse on the farm, for example. The treated biogas exits from the column 710 and is routed to a second polisher 712 for residual H2S removal. The polisher may have a packing of activated carbon for this purpose. The biogas, now substantially free of H2S, is then routed to the inlet of a compressor 714. The compressor pressurizes the biogas to a range, for example of about 10 to about 20 psig. depending upon system configuration. In the illustrated embodiment, the compressed biogas is then cleaned of entrained oil by passing through an oil removal stage 716 that may include therein a packing material through which the biogas must flow and that removes fine suspended oil droplets or oil mist from the biogas. The packing material may be a finely woven metal or textile material that either attracts and knocks out the fine mist of oil droplets or absorbs it onto its surfaces. The polished, oil free biogas then enters into a cooling-dehumidifying system that includes, but is not limited to, the exemplified reheater/precooler 718, air cooler 720, and chiller-exchanger 722. Of course, other types of biogas cooling designs and equipment may also be used. The goal is to first cool the biogas to remove moisture (dehumidify) and thereafter to reheat the dehumidified biogas. As illustrated in the example of FIG. 7. a chiller 725 provides cold fluid to chiller exchanger 722 and the chilling fluid, having taken heat from the biogas, is returned to the chiller for re-cooling and re-use. The chilled biogas from chiller exchanger 722 at about 0° C. is routed to a knock-out drum 724 to remove any (liquid) water condensate from the chilling. The recovered liquid is routed to a sump, and back to the farm for re-use. The chilled biogas in line 726 is routed as a pre-cooling medium to the heat exchanger 718 acting as precooler/reheater to cool the incoming compressed biogas in line 715 that exits from the oil filter 716, while transferring heat to the chilled biogas from line 726. The precooled biogas from precooler/reheater 718 is routed to an air cooler 720, and thence to the chiller 722, as described before. The cold biogas from line 726 that entered the precooler 718, exits in line 719 having been reheated by heat exchange from biogas in line 715 to about 35° C.-40° C., and is routed to packed columns 730 and 732 that operate alternately or in series to treat the biogas to remove contaminants that harm the fuel cell efficiency or its operating life. For example, if there is a residual amount of sulfurous compounds in the biogas, then a scavenger for sulfurous compound will be packed in these columns. Thus, if the residual impurity is COS or another sulfurous compound, a packing of copper oxide, such as finely woven copper oxide that presents a large surface to area ratio, will be packed in the columns. Also useful to remove COS is a packing that is a blend of potassium permanganate with activated carbon. Of course, the two columns 730, 732 may be operated in series and each contain a different material to remove a contaminant. Thus, a material in one column might be activated carbon, and the other might have a copper oxide or potassium permanganate packing.

The high purity biogas, now free of contaminants that can harm the fuel cell, is routed the fuel cell 740 for generation of electricity. As pointed out above, the waste water and CO2 can be reused on the premises. The electricity can be directed at many uses including the grid, battery powering, EV powering, use in municipal or other government facilities as power, and the like.

The foregoing are descriptions of examples of the type of apparatus and the nature of the process flows useful for systems for aggregating and processing of biogas to biomethane. While examples of embodiments of the technology have been presented and described in text, and some examples, by way of illustration, it will be appreciated that various changes and modifications may be made in the described technology without departing from the scope of the inventions, which are set forth in, and only limited by, the scope of the appended patent claims, as properly interpreted and construed.

The invention claimed is:

1. A continuous system of producing electricity directly from biogas, the system comprising:
    an animal manure digester, the digester producing a raw digester gas comprising methane, carbon dioxide and sulfur compounds;
    biogas treatment apparatus configured to continuously treat the raw digester gas to produce biogas, the treatment apparatus removing sulfur compounds from the biogas;
    biogas purification treatment apparatus further processing the biogas to remove compounds deleterious to methane-to-electricity-fuel cell operation, including hydrogen sulfide;
    a solid oxide fuel cell continuously receiving from the biogas purification treatment apparatus a charge of biogas and utilizing the biogas to directly produce electricity; and
    apparatus configured to measure, record and transmit data, to a cloud-based computer system, the data comprising an amount of electrical energy used to charge electrical vehicles and permitting determination of units of electrical charge produced per unit of biogas, and thereby determination of an amount of renewable energy credits attributable to conversion of biogas to electricity.

2. The system of claim 1, wherein the animal manure comprises cow manure.

3. The system of claim 1, wherein the biogas is free of siloxanes.

4. The system of claim 1, wherein the biogas exiting the purification process is free of carbonyl sulfides.

5. The system of claim 1, wherein the biogas has been treated to remove carbonyl sulfides before the fuel cell receives the biogas.

6. The system of claim 5, wherein the biogas purification treatment apparatus further comprises apparatus comprising copper oxide packing configured to treat biogas by removing carbonyl sulfides.

7. The system of claim 1, wherein the solid oxide fuel cell continuously receives a rate of charge of biogas above a minimum turndown rate of the fuel cell.

8. The system of claim 1, further comprising apparatus to convert a direct electrical current produced by the solid oxide fuel cell to alternating current, and apparatus to feed alternating current to an electrical grid.

9. The system of claim 1, wherein the solid oxide fuel cell is configured to produce carbon dioxide and water and the system reuses the water on a farm having the animal manure digester, and uses the carbon dioxide to promote plant photosynthesis.

10. The system of claim 1, comprising a plurality of animal manure digesters, each producing raw digester gas.

11. The system of claim 10, comprising a plurality of animal manure digesters, each producing raw digester gas, wherein the raw digester gas from each of the animal manure digesters is treated in the biogas treatment apparatus to remove hydrogen sulfide and produce a treated biogas, and the treated biogas from each of the digesters is combined and charged as feedstock to the biogas purification apparatus.

12. The system of claim 1 wherein the solid oxide fuel cell operates at 80 to 100% of capacity.

13. The system of claim 1, wherein the biogas comprises up to about 40 mol. % carbon dioxide.

14. The system of claim 1, wherein the biogas received at the solid oxide fuel cell is substantially free of hydrogen sulfide and substantially free of carbonyl sulfide.

15. The system of claim 1, wherein the solid oxide fuel cell operates at temperatures below 750° C.

16. The system of claim 1, wherein transmitting of the data is in real time.

17. The system of claim 16, wherein the real time transmitted data can be used to "book and claim" renewable energy credits in real time.

18. The system of claim 1, wherein the biogas purification treatment apparatus comprises materials to remove carbonyl sulfide from biogas.

19. The system of claim 18, wherein the materials include potassium permanganate.

20. The system of claim 19, wherein the materials include copper oxide.

* * * * *